United States Patent
Otterstedt

(10) Patent No.: US 11,771,792 B2
(45) Date of Patent: Oct. 3, 2023

(54) COMPOSITIONS AND METHODS FOR REDUCING ODOR

(71) Applicant: PREBONA AB, Simrishamn (SE)

(72) Inventor: Jan-Erik Otterstedt

(73) Assignee: PREBONA AB, Simrishamn (SE)

( * ) Notice: Subject to any disclaimer, the term of this patent is extended or adjusted under 35 U.S.C. 154(b) by 491 days.

(21) Appl. No.: 16/770,594

(22) PCT Filed: Dec. 21, 2018

(86) PCT No.: PCT/EP2018/086827
§ 371 (c)(1),
(2) Date: Jun. 6, 2020

(87) PCT Pub. No.: WO2019/122449
PCT Pub. Date: Jun. 27, 2019

(65) Prior Publication Data
US 2020/0289692 A1    Sep. 17, 2020

(30) Foreign Application Priority Data

Dec. 21, 2017  (EP) ..................................... 17209886
Dec. 21, 2017  (EP) ..................................... 17209887

(51) Int. Cl.
*B01D 53/02*      (2006.01)
*A61L 9/014*      (2006.01)
(Continued)

(52) U.S. Cl.
CPC ............. *A61L 9/014* (2013.01); *B01J 20/103* (2013.01); *B01J 20/16* (2013.01);
(Continued)

(58) Field of Classification Search
CPC ...... A61L 2209/22; A61L 9/014; A61L 9/145; B01J 20/02; B01J 20/103; B01J 20/16;
(Continued)

(56) References Cited

U.S. PATENT DOCUMENTS 6,277,408 B1 * 8/2001 Wellinghoff ........... A01N 25/18
                                                      424/473
7,662,354 B2    2/2010 Oki
(Continued)

FOREIGN PATENT DOCUMENTS

JP    2010273698 A    12/2010
KR    2017123009 A *  11/2017 ............. A01N 59/00
(Continued)

OTHER PUBLICATIONS

Translation of KR-2017123009-A, Kim (Year: 2017).*
(Continued)

*Primary Examiner* — Christopher P Jones
(74) *Attorney, Agent, or Firm* — Renner, Otto, Boisselle & Sklar, LLP

(57) ABSTRACT

A method for reducing odor, by providing a colloidal dispersion of particles of silica having a particle size of from 3 nm to 100 nm, said particles having ions of one or more metals selected from copper, silver, zinc and iron adsorbed at the particle surface, and bringing at least one of said particles into contact with an odorous compound; and/or providing an aqueous silicate solution containing metal ions selected from ions of copper, silver, zinc and iron, and bringing at least one metal ion-carrying silicate particle formed in the solution into contact with an odorous compound. A composition for use in such a method and a product treated by such a composition.

12 Claims, 1 Drawing Sheet

(51) Int. Cl.
  *B01J 20/10* (2006.01)
  *B01J 20/16* (2006.01)
  *B01J 20/28* (2006.01)
  *B01J 20/32* (2006.01)
  *C09D 1/00* (2006.01)
  *D06M 11/78* (2006.01)
  *D06M 11/79* (2006.01)
  *D06M 11/83* (2006.01)
  *D06M 101/32* (2006.01)

(52) U.S. Cl.
  CPC ... *B01J 20/28007* (2013.01); *B01J 20/28028* (2013.01); *B01J 20/3236* (2013.01); *B01J 20/3293* (2013.01); *C09D 1/00* (2013.01); *D06M 11/78* (2013.01); *D06M 11/79* (2013.01); *D06M 11/83* (2013.01); *A61L 2209/22* (2013.01); *D06M 2101/32* (2013.01); *D06M 2400/01* (2013.01)

(58) Field of Classification Search
  CPC ............ B01J 20/28007; B01J 20/28028; B01J 20/3236; B01J 20/3293; C01B 33/14; C01B 33/20; D06M 11/78; D06M 11/79; D06M 11/83; A01N 59/16
  See application file for complete search history.

(56) References Cited

U.S. PATENT DOCUMENTS

| | | |
|---|---|---|
| 2005/0084438 A1 | 4/2005 | Do et al. |
| 2005/0084632 A1 | 4/2005 | Urlaub et al. |
| 2008/0194447 A1* | 8/2008 | Oki ............... A61Q 15/00 510/131 |
| 2017/0333588 A1* | 11/2017 | Miyamura ........... B01J 20/0237 |
| 2020/0239322 A1 | 7/2020 | Otterstedt et al. |

FOREIGN PATENT DOCUMENTS

| | | |
|---|---|---|
| WO | 2003092885 A1 | 11/2003 |
| WO | 2005014059 A1 | 2/2005 |
| WO | 2011037523 A1 | 3/2011 |
| WO | 2015095608 A1 | 6/2015 |
| WO | 2017216285 A1 | 12/2017 |
| WO | 2019020576 A1 | 1/2019 |

OTHER PUBLICATIONS

International Search Report and Written Opinion for International Application No. PCT/EP2018/086827 dated May 23, 2019.
Zeta Potential Analysis of Antiparticles, nanoComposix, Sep. 2012, V.1.1 San Diego, California.

* cited by examiner

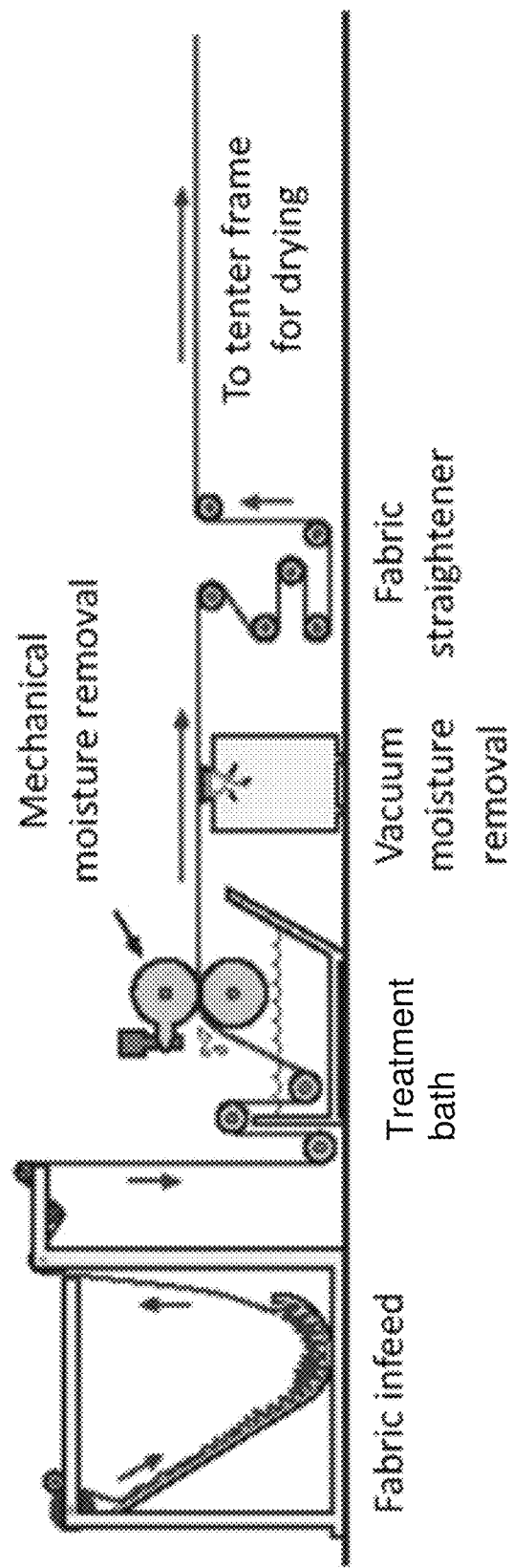

COMPOSITIONS AND METHODS FOR REDUCING ODOR

This application is a national phase of International Application No. PCT/EP2018/086827 filed Dec. 21, 2018 and published in the English language, which claims priority to European Patent Application No. 17209887.3 filed Dec. 21, 2017 and European Patent Application No. 17209886.5, all of which are hereby incorporated herein by reference.

FIELD OF THE INVENTION

The present invention relates to compositions containing metal ions for use in methods of reducing odor. In particular, the invention relates to colloidal dispersions containing metal ions, and their use, in particular in methods for reducing odor. The invention furthermore relates to metal containing silicate solutions, and their use in methods for reducing odor. The invention also relates to the use of materials comprising silica nanoparticles to which metal ions have been adsorbed, in methods for reducing odor. It also relates to processes for reducing odor by bringing such colloidal dispersions or solutions into contact with odorous compounds.

BACKGROUND AND PRIOR ART

Foul smell and malodor may cause discomfort in various confined spaces such as restrooms, public toilets, industrial settings plants etc. In some cases, use is made of odor masking devices, such as toilet perfumes. It would be preferable to provide a means for efficiently reducing the level of odorous compounds or reduce the source of odor.

International patent application No. PCT/SE2010/051007 (WO 2011/037523), incorporated herein by reference, discloses a colloidal dispersion comprising carrier particles of silica having a particle size from 3 nm to 100 nm to which silver ions have been adsorbed.

International patent application No. PCT/EP2017/064658 (WO 2017/216285), incorporated herein by reference, discloses a colloidal dispersion of particles of silica having a particle size of from 3 nm to 100 nm, to which ions of one or more metals are adsorbed, selected from metals having atomic numbers 21-31, 39-46, 48-50, 57-82, and 89-93, and a method for preparing the dispersion.

International patent application No. PCT/EP2018/069941 (not yet published), incorporated herein by reference, aqueous silicate solution containing ions of a metal having an atomic number selected from atomic numbers 21-31, 39-50, 57-82, and 89-93, a process for preparing such a solution, and its use in e.g. paints and sealants.

SUMMARY OF THE INVENTION

In a first aspect, a method is provided for reducing odor by bringing a colloidal dispersion as described herein into contact with an odorous compound. The colloidal dispersion is a stable colloidal dispersion comprising silica nanoparticles and metal ions, e.g. metal ions selected from copper, silver, zinc and iron ions.

In a further aspect, a method is provided for reducing odor by bringing a metal containing silicate solution as described herein into contact with an odorous compound.

In some embodiments, a method is provided for reducing odor in a confined space, e.g. a room, a building, a tunnel, a duct, a box, a cupboard, etc.

Some embodiments relate to a method for reducing the level of odorous contaminants in a confined space, such as a room, a building, or any other confined space where presence of malodorous airborne matter or compounds may cause discomfort.

In the following description, a reference to a "colloidal dispersion" according to the invention, should also be understood as a reference to a "metal containing silicate solution", unless otherwise indicated or apparent from the context. In some embodiments, the colloidal dispersion is a dispersion of silica particles having a size of from 3 to 100 nm to which metal ions are attached, as described herein. In some other embodiments, the "colloidal dispersion" is a metal containing silicate solution as described herein. In some further embodiments, the "colloidal dispersion" comprises both a dispersion of silica particles having a size of from 3 to 100 nm to which metal ions are attached and a metal containing silicate solution.

Some embodiments relate to methods for treating air in ducts, living space and other enclosed space so as to achieve odor control e.g. by spraying a composition (or sol) as disclosed herein into the air of the enclosure, e.g. a sol containing ions of one or more metals selected from copper (Cu), silver (Ag), iron (Fe) and zinc (Zn). Furthermore, the sols described herein may be used as coatings or impregnations on surfaces of e.g. textiles, walls, or materials used in air filters or other parts that come into contact with air, in e.g. air ducts, to reduce the amount of odorous compounds in the air.

In some aspects, therefore, a method for reducing malodor in a confined space is provided, comprising bringing the colloidal dispersion (also referred to as a sol) disclosed herein into contact with air in the confined space. The sol may be brought into contact with air by any means, e.g. by spraying directly into the air or by applying the sol onto a surface in contact with air in the confined space or which surface is brought into contact with air in the confined space, e.g. a wall, ceiling, furniture, toilet basins, floor, textiles, carpet, curtains, air filter, etc.

In some aspects, a method is provided for deodorization of a solid material, such as a textile, fiber web, or a porous material, comprising brining the solid material in contact with the sol disclosed herein. For example, malodor or risk of malodor in a solid material may be reduced by applying the sol defined herein to the material by any means, e.g. by dipping the material in the sol, spraying the sol onto the material, brushing the sol onto the material etc.

In some embodiments, the methods disclosed herein are performed by use of a colloidal dispersion (sol) of particles of silica having a particle size of from 3 nm to 100 nm, said particles carrying ions of one or more metals at the particle surface, selected from Cu, Ag, Zn, and Fe.

Thus, further provided herein is a colloidal dispersion of particles of silica having a particle size of from 3 nm to 100 nm, said particles carrying ions of one or more metals at the particle surface, selected from Cu, Ag, Zn, and Fe, and the use of such dispersion in a method as mentioned herein, e.g. a method for reducing odor.

In some embodiments, a process is provided comprising preparing a colloidal dispersion, by admixing a silica sol and one or more solutions of one or more salts of Cu, Ag, Zn, and Fe, so as to obtain a colloidal dispersion of silica particles carrying metal ions at the surface of said silica particles, and using the colloidal dispersion thus obtained in a method for reducing odor.

In some embodiments, use is made of a mixture of colloidal dispersions of silica particles (also referred to herein as "silica sols") where the metal ions adsorbed on each component sol are different, e.g. a mixture of one silica sol having one type of metal ions, selected from Cu, Ag, Zn, and Fe ions, adsorbed at the surface of the silica particles, and another silica sol having another type of metal ions adsorbed at the surface of the silica particles. The other type of metal ions may be selected also from Cu, Ag, Zn and Fe ions, but in some embodiments is selected from other metal ions, e.g. other transition metals.

In yet another embodiment use is made of a mixture of silica sols of different particle sizes obtained by blending silica sols of different particle sizes with the same or different metal ions, e.g. selected from Cu, Ag, Zn, and Fe ions, adsorbed on the surface of the particles.

In some embodiments, a stable colloidal dispersion is used containing silica nanoparticles having at least one metal ion selected from Cu, Ag, Zn, and Fe ions adsorbed at the surface and optionally also having another metal ion adsorbed at the surface.

Very advantageously, colloids with high concentrations of multivalent metals, e.g. multivalent transition metals or lanthanides, can be achieved according to the present invention.

The particle size and particle size distribution of the colloidal dispersion used herein can be tailor made to meet narrow specifications.

Finally, further provided herein is a stable colloidal dispersion containing particles of silica having a particle size of from 3 nm to 100 nm, said particles having ions of one or more metals selected from copper, silver, zinc and iron adsorbed at the particle surface.

In some embodiments, the colloidal dispersion is or comprises an aqueous silicate solution containing ions of one or more metals selected from Fe, Cu, Zn or Ag.

BRIEF DESCRIPTION OF THE DRAWINGS

FIG. 1 represents a textile mill set-up used in a method of treatment of a fabric with a formulation of the invention.

DETAILED DESCRIPTION OF THE INVENTION

The Silica Sol

The particles of the silica sols used to prepare the materials of the present invention carry an anionic charge and the sols are anionic sols.

A convenient source of the silica particles of the present invention are commercial silica sols. Such sols are aqueous dispersions of silica particles and the particles are uniform spheres of silica, which have no internal surface area or detectable crystallinity. They are usually dispersed in an alkaline medium, which reacts with the silica surface to produce a negative charge. Because of the negative charge, the particles repel one another resulting in a stable product.

In some commercial products, the particle surface is modified with aluminosilicate ions so as to provide the surface with a fixed, pH-independent negative charge that will make the products more stable towards gelling than the sols from which they were prepared. Trivalent aluminium atoms have been substituted for part of the tetravalent silicon atoms in the surface of the particles, creating a fixed negative charge which is independent of pH. The surface coverage of Al is much less than that corresponding to a Langmuir monolayer.

The solids content of the sol depends on the particle size and varies from less than 10% by weight silica for the smallest particles, 3 nm, to about 50% by weight silica for larger particles, >20 nm. The surface of the particles in aqueous silica sols is covered with surface hydroxyl groups, silanol groups. The particle size of the silica sols used according to the present invention is typically in the range of 3-100, preferably 4-50 nm, more preferably 5-25 nm, even more preferably 5-15 nm, e.g. 5-12 nm, or 5-10 nm. The silica sols preferably have a specific surface area (e.g. by SEARS's titration or BET) of typically 20-1000 $m^2/g$, preferably 30-800 $m^2/g$, more preferably 100-600 $m^2/g$, even more preferably 200-600 $m^2/g$, and most preferably 200-550 $m^2/g$.

Stabilization of commercial silica sols is generally accomplished by adjusting the pH of the sol to between 8.0 and 10.0, normally by addition of alkali, usually a solution of sodium hydroxide. The sols also contain small amounts of other electrolytes such as sodium chloride and sodium sulfate.

The stability of highly concentrated silica sols is very sensitive to the presence of electrolytes. The electrolyte concentration can be reduced to a minimum by using ion exchange resins. The composite sols of the present invention may be prepared by use of commercial silica sols, or commercial silica sols modified, for instance by treating the sols with sodium aluminate solution so as to create aluminosilicate sites on the particle surface in order to obtain a silica sol that is stable in the pH range of 3-12, more particularly 4-11, by methods well known to the person of ordinary skill.

Thus, in some embodiments, at least some of the silica particles of the composite sol of the invention have aluminosilicate sites at the particle surface.

A convenient way to introduce aluminosilicate sites on the surface of colloidal silica is to use weak acid cation resin to remove sodium ions from the silica sol—sodium aluminate system and thus bring about reaction of the aluminate ions with the silica surface. In this system, pH will usually not fall below pH 5 even if an excess of weak acid cation exchange resin is used.

A calculated amount of sodium aluminate solution to give the desired number of aluminosilicate sites per $nm^2$ particle surface is simply added to the slurry of colloidal silica and resin.

The creation of aluminosilicate sites on the surface of silica is well described in the literature, (e.g. in Iler, The Chemistry of Silica, 1979, pp. 407-409). Such descriptions also indicate that it is difficult to introduce much more than about 2 aluminosilicate sites per $nm^2$ silica surface, for example.

When using aluminized silica particles in the composite sols of the invention, the concentration of aluminosilicate sites on the surface of the silica particles falls in the range from about 0.2 site per $nm^2$ to about 2.0 sites per $nm^2$, e.g. 0.30-1.50, or 0.3-1.25, or 0.4-1.0 site per $nm^2$, e.g. 0.4-0.8 site per $nm^2$.

Stability

The term stable used in the present invention means that the product should be stable toward gelling, implying that the relative viscosity should not increase more than 100% (e.g. from 5 to 10 mPas) under a period of about two months. The term also means stability toward precipitation; i.e. there is no substantial precipitation of solid content, characterised by that no more than 20% of the solid material has precipitated and settled as a sludge at the bottom, if stored under normal (e.g. ambient or optionally protected from light) conditions, for a period of two months.

The Metal Ion

The metal used according to the present invention preferably is selected from Cu, Ag, Fe and Zn, more preferably from Cu and Ag. In some embodiments, the metal used is Cu. In some other embodiments, the metal used is Ag. In some embodiments, the metal is one which may exist in more than one oxidation state, e.g. Cu or Fe. In some embodiments, the metal is selected from Cu, Fe and Zn, e.g. from Cu and Zn.

If further metal ions are present in the colloidal dispersion of the invention, the metals e.g. may be selected from Sc, Ti, V, Cr, Mn, Co, Ni, and Ga.

Nano-composite materials for use according to the present invention are prepared by contacting a non-metallic carrier material in the form of e.g. colloidal silica with a solution comprising the metals ions as specified herein. The reactants and products used in the various preparations and methods fall in the domain of colloids and colloid chemistry and due care has to be taken concerning concentration of reactants and products, maintaining a high electrical charge on colloidal particles, using water of good quality, preferably deionised water, observing proper rate of addition and order of addition of the components, working in conservative but realistic temperature ranges and providing sufficient agitation and stirring so as to maintain stability towards gelling or aggregation of reactants and products. Selecting and optimizing conditions of the beforementioned type are considered to be within the capacity of the person of ordinary skill in the art, in light of the present description and the embodying examples.

The colloidal silica sol used to prepare the composite sol of the invention of the present invention generally has a concentration of from 0.1% by weight of $SiO_2$ or less to undiluted sols that could contain 50% by weight of $SiO_2$ or more.

Most soluble salts of the metals mentioned as useful herein above, can be used to prepare the materials of the present invention.

So as to achieve strong adsorption (attachment) of metal ions on the surface of nano-sized carrier particles the electrical charge of the latter should be high but of opposite sign to that of the metal ions.

The charge on the particles of colloidal silica or on particles of silica in an aqueous environment increases exponentially with pH and is almost 0.5 units of negative charge per $nm^2$ particle surface at a pH of about 10 and at very low, $10^{-4}$ normal, electrolyte concentrations. Colloidal silica has a local stability maximum at the point of zero charge, which occurs at about pH 2.0. The stability of a silica sol first decreases with pH and reaches a minimum around pH 6, after which the sol enters a region of high stability between pH 8 and pH 11.

The stability towards gelling and flocculation, of solutions of in particular transition metals in water is quite sensitive to pH. If pH is raised a few units above the natural pH of the solution gelling and/or flocculation will occur. In experiments performed by the inventor, most solutions of transition metals required the addition of only a few, say 3-5, drops of 1 M NaOH before flocs could be seen in the solutions (the sample size was typically 50 g and a drop from a plastic pipette typically weighed 0.025 g). The exact value of pH at which formation of flocs becomes visible to the naked eye depends on the type and concentration of metal in the solution.

Although silica sols are stable over a wide pH range it is preferable to prepare the formulations of the invention in the pH region of 8-12, more particularly 9-11, where silica sols are most stable.

The concentration of the metal solutions used according to the present inventions is preferably in the range of from about 0.1 mM ($10^{-4}$ mol/L) to about 200 mM, e.g. from about 0.2 mM to about 100 mM, e.g. from about 0.5 mM to about 50 mM, or from about 1 mM to about 20 mM, or from about 2 mM to about 10 mM, although both higher and lower concentrations are contemplated as possible. The concentration of the metal in the composite sol will be somewhat lower due to the diluting effect of mixing the metal solution with the silica sol. Thus, composite sols may be prepared according to the invention that contain from about 0.01 mM metal cation or less, to about 100 mM metal cation or more, e.g. about 0.05 mM to about 50 mM, or about 0.1 mM to about 40 mM, or about 0.5 mM to about 30 mM, or about 1 mM to about 10 mM cation of metal(s) of the invention.

In some embodiments, the silica sols used contain aluminosilicate-modified silica particles. Adsorption of metal cations on aluminosilicate-modified silica sols can be carried out over a wide pH range, e.g. from about pH of about 3 to a pH of about 12, e.g. from a pH of about 4 to a pH of about 11.5, or a pH of about 5 to a pH of about 11, e.g. a pH of about 6 to a pH of about 10.5. However, it is preferable to carry out the adsorption in the pH range where silica sols are most stable, that is the alkaline range, for instance in the pH range from about 8 to about 11, e.g. about 8 to 10.5.

The pH can be controlled at different steps of the process for making the composite sols of the invention. In most of the examples as described herein below, the silica sol was added to the metal salt solution and the pH was then adjusted to between 10 and 11 by adding 1 M NaOH-solution to the metal containing silica sol. Alternatively, alkali can be added to the silica sol before said sol is added to the metal salt solution or before the metal salt solution is added to said sol.

The rate at which metal salt solution can be admixed with the silica sol without destabilizing the sol depends on the conditions being used in the preparation. The rate of addition can be fast as long as the increments of added salt are rapidly dispersed throughout the sol, or vice verse. However, the robustness of the colloidal systems according to the present invention is quite surprising. In many of the small scale preparations it is actually possible to inject silica sol into a magnetically stirred metal salt solution in very short times, for instance less than 10 to 15 seconds, without destabilizing the sol. However, in most of the small scale laboratory preparations, for instance preparations of sols containing about 1000 ppm of metal, longer addition times, typically 2 to 3 minutes were used so as to be on the safe side in terms of having good stability towards gelling or aggregation. Similar time scales will apply to larger scale preparations provided that sufficient agitation or stirring is used.

In the present specification, any ppm value is calculated based on a weight basis. Thus, e.g. in a solution of metal ion containing n ppm metal, there is n mg metal present per kg of solution. Likewise, in a silica sol containing n ppm metal, there is n mg metal present per kg of the metal-containing silica sol.

For the purpose of the present invention, and unless otherwise specified or apparent from the context, "metal" refers to a metal selected from copper, silver, iron and zinc, preferably copper and silver.

A sol of a given concentration of the selected metal can be prepared in different ways. In one method, a certain amount of the metal solution is added to a silica sol with specified values of particle size and concentration of silica. In another method, the same amount of the metal solution is added to a sol of the same particle size but higher, for instance four times higher, concentration of silica. The overall concentration of the selected metal is the same in the two sols but the concentration of metal on the particle surface of the former sol is higher—four times higher—than that of the latter sol. Thus, a material of the present invention with a given, overall concentration of metal and a given particle size can be obtained by combining high concentration of particles, that is high concentration of silica, with low concentration of metal on the particle surfaces or by combining high surface concentration of metal with low silica concentration.

The concentration of $SiO_2$ of the composite sol of the present invention generally ranges from about 0.001% by weight, e.g. about 0.005% by weight, or about 0.01% by weight, or about 0.05% by weight, or about 0.1% by weight, or about 0.5% by weight, or about 1% by weight, or about 2% by weight, to about 25% by weight, or about 20% by weight, or about 15% by weight, or about 10% by weight of $SiO_2$, or about 8% by weight, or about 5% by weight, the remaining part (adding up to 100%) normally comprising the selected metal ion(s) and water. For example, in some embodiments, the concentration of $SiO_2$ of the composite sol of the present invention ranges from about 0.005% by weight to about 15% by weight, e.g. from about 0.1% by weight to about 10% by weight, or from about 0.5% by weight to about 5% by weight.

Metal Population on Particle Surface

Knowing the concentration of metal in the sol, the atomic weight of the metal in question, the specific surface area of the silica particles and concentration of silica in weight percent, the surface concentration, $C_s$, of metal atoms (ions) per $nm^2$ of $SiO_2$ particle surface, can be calculated according to equation (1):

$$C_s = 60 M_1 / (M_{met} A K) = (60/AK)(M_1/M_{met}) \quad (1)$$

wherein $M_1$ is the concentration of metal in the sol, in ppm, $M_{met}$ is the atomic weight of the metal, in g, A is the specific surface area of the sol particles, in $m^2/g$, and K is the concentration of silica in weight percent The concentration of metal ions on the surface of the ultimate particles making up the materials of this invention falls in the range from about 0.0005, or from about 0.004, or from about 0.005, or from about 0.006, or from about 0.008, or from about 0.01, or from about 0.02, or from about 0.03, or from about 0.04, or from about 0.05, or from about 0.08, or from about 0.1 metal ion per $nm^2$ to about 5, or to about 4, or to about 3, or to about 2 metal ions per $nm^2$, e.g. to about 1 metal ion per $nm^2$. In some embodiments, the concentration of metal ions on the particle surface of the colloidal silica sol of the invention ranges from about 0.01 metal ion per $nm^2$ to about 2 metal ions per $nm^2$, e.g. about 0.01 to about 1 metal ion per $nm^2$, or about 0.05 to about 1 metal ion per $nm^2$, more preferably about 0.1 to about 0.8 metal ion per $nm^2$.

In the case of silica particles having aluminosilicate sites at the surface, it is considered that typically one metal ion adsorbs on one Al—Si-site, but not all Al—Si sites may have adsorbed transition metal species adsorbed on them. The ratio by number between metal ions and Al—Si sites may vary within the range of from 0.01 to about 1.0, but is preferably between 0.05 and 0.8, e.g. between 0.1 and 0.6.

By "adsorption" according to the present invention is meant that the metal ion attaches to the surface, whether by electrostatic or ionic bonding or any other type of bonding, e.g. partly covalent bonding. The adsorption of metal ions on the surface of the silica particles may be monitored by measuring the Zeta potential of the colloidal sol.

The load of metal ions vs. silica particles may be expressed as number of metal cations per unit of surface area of the silica particles. This is the "specific metal load" or surface concentration of the metal cation $c_s$.

The load of metal ion vs. silica particles in the composite sol may also be expressed as the number of metal ions $n_m$ for each silica particle. However, for very low metal loads, it may be more meaningful to express the relationship between the number of metal ions and number of particles in the silica sol as the inverse of the number of metal ions for each silica particle, i.e. $n_m^{-1}$.

The relationship between $n_m^{-1}$ and $c_s$ is given by the equation (2):

$$n_m^{-1} = \frac{1}{n_m} * \frac{A_p}{A_p} = \frac{1}{c_s * A_p} \quad (2)$$

wherein $n_m$, is the number of metal ions per silica particle in the composite sol, $A_p$ is the surface area of one silica particle in the composite sol, and $c_s$ is the surface concentration of metal ions at the surface of the silica particle.

Equation (2) shows that $n_m^{-1}$ is inversely proportional to the surface area $A_p$ of the particle and the surface concentration $c_s$ of metal ions at the surface of the silica particles.

For $c_s$=0.0005 ions/$nm^2$, Table 1 illustrates how $n_m^{-1}$, viz. the number of silica particles per ion, varies as a function of the silica particle diameter.

TABLE 1

Number of silica particles per metal ion as a function of particle diameter in a composite sol, $c_s$ = 0.0005 ions/$nm^2$

| Particle diameter (nm) | number of particles per ion |
|---|---|
| 5 | 25 |
| 7 | 13 |
| 12 | 4.4 |
| 22 | 1.3 |

As may be seen from Table 1, at $c_s$=0.0005 ions/$nm^2$ and a particle diameter of 5 nm, 4 out of 100 silica particles in the composite sol of the invention carry a metal cation, viz. there are 25 particles present for each metal ion in the composite sol.

In other words, the number ratio between metal ions and silica particles in the composite sol of the present invention may vary from high values, where more than one metal ion is present for each silica nanoparticle, e.g. more than 10 metal ions are present for each silica nanoparticle, to low values, where more than one silica nanoparticle is present for each metal ion, e.g. more than 10 silica nanoparticles are present for each metal ion.

In some embodiments, the metal ion is present at the surface of the nanoparticle at a (mean) surface concentration of at least 0.0005 ion/$nm^2$, at least 0.001 ion/$nm^2$, at least 0.005 ion/$nm^2$, at least 0.01 metal ion/$nm^2$, at least 0.02 metal ion/$nm^2$, at least 0.05 metal ion/$nm^2$, at least 0.08 metal ion/nm$^2$, or at least 0.1 metal ion/nm$^2$; and at most 5 metal ions/nm$^2$, at most 2 metal ions/nm$^2$, at most 1 metal ion/nm$^2$, at most 0.8 metal ion/nm$^2$, at most 0.6 metal ion/nm$^2$, at most 0.4 metal ion/nm$^2$, at most 0.2 metal ion/nm$^2$; or at most 0.15 metal ion/nm$^2$.

In some embodiments, the metal ion is present at the surface of the nanoparticle, at a surface concentration ranging from 0.0005 to 0.8 metal ion/nm$^2$, from 0.001 to 0.8 metal ion/nm$^2$, or from 0.005 to 0.8 metal ion/nm$^2$; e.g. from 0.0005 to 0.5 metal ion/nm$^2$, from 0.001 to 0.5 metal ion/nm$^2$; from 0.0005 to 0.2 metal ion/nm$^2$, from 0.001 to 0.2 metal ion/nm$^2$, or from 0.005 to 0.2 metal ion/nm$^2$.

In some embodiments, the metal ion is present at the surface of the nanoparticle, at a surface concentration ranging from 0.01 to 0.8 metal ion/nm$^2$, e.g. from 0.02 to 0.8 metal ion/nm$^2$, from 0.04 to 0.8 metal ion/nm$^2$, from 0.06 to 0.8 metal ion/nm$^2$, or from 0.08 to 0.8 metal ion/nm$^2$.

In some embodiments, the metal ion is present at the surface of the nanoparticle, at a surface concentration ranging from 0.01 to 0.5 metal ion/nm$^2$, e.g. from 0.02 to 0.5 metal ion/nm$^2$, from 0.04 to 0.5 metal ion/nm$^2$, from 0.06 to 0.5 metal ion/nm$^2$, or from 0.08 to 0.5 metal ion/nm$^2$.

In some embodiments, the metal ion is present at the surface of the nanoparticle, at a surface concentration ranging from 0.01 to 0.2 metal ion/nm$^2$, e.g. from 0.02 to 0.2 metal ion/nm$^2$, from 0.04 to 0.2 metal ion/nm$^2$, from 0.06 to 0.2 metal ion/nm$^2$, or from 0.08 to 0.2 metal ion/nm$^2$.

In some embodiments, the metal ion is present at the surface of the nanoparticle, at a surface concentration ranging from 0.01 to 0.15 metal ion/nm$^2$, e.g. from 0.02 to 0.15 metal ion/nm$^2$, from 0.04 to 0.15 metal ion/nm$^2$, from 0.06 to 0.15 metal ion/nm$^2$, or from 0.08 to 0.15 metal ion/nm$^2$.

In some embodiments, the metal ion is present at the surface of the nanoparticle, at a surface concentration ranging from 0.01 to 0.12 metal ion/nm$^2$, e.g. from 0.02 to 0.12 metal ion/nm$^2$, from 0.04 to 0.12 metal ion/nm$^2$, from 0.06 to 0.12 metal ion/nm$^2$, or from 0.08 to 0.12 metal ion/nm$^2$.

In some embodiments, the metal ion is present at the surface of the nanoparticle, at a surface concentration ranging from 0.01 to 0.1 metal ion/nm$^2$, e.g. from 0.02 to 0.1 metal ion/nm$^2$, from 0.04 to 0.1 metal ion/nm$^2$, from 0.06 to 0.1 metal ion/nm$^2$, or from 0.08 to 0.1 metal ion/nm$^2$.

In some embodiments, the colloidal dispersion contains from 100 ppm to 1000 ppm by weight of metal ion, from 1% to 20% by weight of $SiO_2$, the silica particles having a size of from 3 nm to 50 nm.

In some embodiments, the colloidal dispersion contains from 100 ppm to 500 ppm by weight of metal ion, from 2% to 10% by weight of $SiO_2$, and the silica particles therein have a size of from 3 nm to 20 nm.

In some embodiments, the colloidal dispersion contains from 200 ppm to 500 ppm by weight of metal ion, from 2% to 8% by weight of $SiO_2$, and the silica particles therein have a size of from 3 nm to 10 nm.

In some embodiments, the colloidal dispersion contains from 200 ppm to 400 ppm by weight of metal ion, from 3% to 7% by weight of $SiO_2$, and the silica particles therein have a size of from 3 nm to 7 nm; for example, a colloidal dispersion as defined herein may contain about 300 ppm by weight of metal ion, about 5% by weight of $SiO_2$, the silica particles having a size of about 5 nm. In some of these embodiments, the metal is selected from copper ($Cu^{2+}$), silver (Ag+) and zinc ($Zn^{2+}$). In some other of these embodiments, the metal is selected from copper ($Cu^{2+}$), silver (Ag+) and iron ($Fe^{2+}$ and $Fe^{3+}$, in particular $Fe^{3+}$). In some embodiments, the metal is copper ($Cu^{2+}$). In some other embodiments, the metal is silver ($Ag^+$). In still other embodiments, the metal is zinc ($Zn^{2+}$). In still other embodiments, the metal is iron ($Fe^{2+}$ or $Fe^{3+}$, in particular $Fe^{3+}$).

In some embodiments, the molar ratio of the metal ions and the silica particles (i.e. number of ions per particle) is from 1 to 20, or from 1 to less than 10, e.g. from 1 to 9, from 1 to 8, from 1 to 7, from 1 to 6, from 1 to 5, from 1 to 4, or from 1 to 3. In some of these embodiments, the molar ratio is at least 9, or at least 8, or at least 7, or at least 6, or at least 5, or at least 4, or at least 3, or at least 2.

In still other of these embodiments, more than one metal is present in the colloidal dispersion, e.g. the metal is a mixture of silver and copper.

The carrier liquid of the colloidal dispersion normally is deionized water. However, if suitable, other liquids, e.g. organic solvents, also may be included.

The Metal Containing Silicate Solutions

The silicate solutions used according to the present invention are "non-true solutions" or "colloidal solutions". Depending on e.g. the silicate concentration, at least a portion of the silicate is not dissolved on a molecular level but may form oligomers of different size.

The silicate used according to the invention may be e.g. an alkali silicate or a quaternary ammonium silicate. In some embodiments, the silicate of the invention is an alkali silicate. In some other embodiments, the silicate is a quaternary ammonium silicate.

In some embodiments, the silicate is a quaternary ammonium silicate containing ammonium ions of the type $R_4N^+$ wherein each R is independently selected aliphatic or aromatic groups, e.g. C1-C6 alkyl groups or phenyl, optionally carrying other functional groups, such as hydroxyl functions. For example, in some embodiments, the quaternary ammonium silicate is a tetraalkyl ammonium silicate, wherein the alkyl groups e.g. may contain from 1 to 6 carbon atoms, or from 1 to 3 carbon atoms, e.g. the alkyl groups may be methyl groups. A quaternary ammonium silicate useful according to the invention may be prepared as described in U.S. Pat. No. 9,695,111, the teachings of which are incorporated herein by reference.

Commercial solutions of silicates also are a convenient source of the soluble silicates of the present invention. For example, in some embodiments, the silicate solution a commercially available alkali silicate solution, such as sold by e.g. PQ Corporation (www.pqcorp.com).

In alkali silicate solutions, the key variables are the alkali metal, generally lithium (Li), sodium (Na) or potassium (K); the ratio of $SiO_2$ to alkali metal oxide in the silicate, and the concentration of the silicate in the solution.

The ratio of $SiO_2$ to alkali metal oxide ($SiO_2/M_2O$) may be expressed as a weight ratio or molar ratio. In the case of sodium silicate the two ratios are nearly the same. Thus a weight ratio of a sodium silicate is transformed to the mole ratio by the multiplication factor 1.03; for potassium silicate the weight ratio is multiplied by the factor 1.57 to give the mole ratio. For lithium silicate the factor is 0.50.

For sodium silicates, the $SiO_2/Na_2O$ weight ratio ranges from about 1.6 to about 4.

The $SiO_2/K_2O$ ratio of potassium silicates varies from about 1.5 to about 2.5 on a weight basis, which corresponds to a ratio of from 2.3 to 3.8 on a molar basis.

The $SiO_2/Li_2O$ ratio of lithium silicates varies from about 6.0 to about 20.0 on a weight basis, which corresponds to a ratio of from about 3.0 to about 10.0 on a molar basis.

During the development of concentrated silica sols stabilized with NaOH it was realized that in the $SiO_2/Na_2O$ ratio range of about 4:1 to 25:1 the concentrated compositions were generally unstable, and eventually gelled. When a 3.25 ratio sodium silicate solution was added to a concentrated silica sol to reduce the $SiO_2/Na_2O$ ratio from 100:1 to 5:1, for example, a gel immediately formed. However, it was discovered that by aging or warming the gel, a stable solution was again formed. Thus silicate solutions having $SiO_2/Na_2O$ weight ratios of from 4.2:1 to 6:1 containing 10-30% $SiO_2$ could be prepared from silica sols originally containing 5-25 nm particles.

If instead a 3.25 ($SiO_2/K_2O$) molar ratio potassium silicate is added to an alkali-stabilized, concentrated silica sol, gelling does not occur. Thus, stable mixtures of colloidal silica and potassium silicate can be prepared with a silica concentration of 15-30 wt. % and $SiO_2/K_2O$ molar ratios of 11:1 to 24:1.

Similarly, stable mixtures of colloidal silica and lithium silicate can be prepared with a silica concentration of 15-30 wt. % and $SiO_2/Li_2O$ molar ratios of 4:1 to 25:1.

Alkali silicate solutions generally contain both silicate ions and colloidal polymeric (including oligomeric) silicate species, formed by polymerization of the monomeric $SO_4^{4-}$ unit to form siloxane (Si—O—Si) bonds. The polymeric species, which may be linear or cyclic, are not of uniform size. The degree of polymerization generally increases with increasing $SiO_2/Me_2O$ ratio and with increasing concentration of the silicate.

Generally, the term "silicate solution" as used herein refers to a liquid phase containing polymeric (including oligomeric) silicate species, although it should be realized that some of the silicate may also be present as dissolved non-polymeric species.

In some embodiments, therefore, the formulation according to the invention contains sodium silicate having a $SiO_2/Na_2O$ molar ratio of about 6:1 to about 2:1, at a $SiO_2$ concentration of about 2% by weight to about 30% by weight, based on the total weight of the formulation.

In some embodiments, the formulation according to the invention contains potassium silicate having a $SiO_2/K_2O$ molar ratio of about 2:1 to about 25:1 at a $SiO_2$ concentration of about 2 by weight to about 30% by weight, based on the total weight of the formulation.

In some embodiments, the formulation according to the invention contains lithium silicate in a $SiO_2/Li_2O$ molar ratio of about 2:1 to about 25:1 at a $SiO_2$ concentration of about 2% by weight to about 30% by weight, based on the total weight of the formulation.

In some further embodiments, the formulation according to the invention contains a more than one type of silicate, e.g. more than one type of quaternary ammonium silicate, or more than one type of alkali silicate, or a mixture thereof. For example, in some embodiments, the formulation contains lithium silicate and at least one other type of silicate, selected from sodium silicate and potassium silicate. In some embodiments, the formulation contains sodium silicate and at least one other type of silicate, selected from lithium silicate and potassium silicate. In some embodiments, the formulation contains potassium silicate and at least one other type of silicate, selected from lithium silicate and sodium silicate.

In some embodiments, the formulation contains lithium silicate and sodium silicate. In some other embodiments, the formulation contains lithium silicate and potassium silicate. In some other embodiments, the formulation contains sodium silicate and potassium silicate.

The formulation of contains one or more metals selected from Fe (iron), Cu (copper), Zn (zinc), and Ag (silver). Generally, said metal is present in the formulation in a total amount of from 1 to 5000 ppm (all ppm values are by weight) of the formulation, e.g. from 10 to 5000 ppm. In some embodiments, the metal is present in an amount of from 10 to 4000 ppm, e.g. from 10 to 3500 ppm, from 10 to 3000 ppm, from 10 to 2500 ppm, from 10 to 2000 ppm, from 10 to 1500 ppm, from 10 to 1000 ppm, from 10 to 800 ppm, or from 10 to 700 ppm, or from 10 to 500 ppm.

The "metal" in the inventive formulation as mentioned herein above is Fe, Cu, Zn or Ag, i.e. it does not include an alkali metal, e.g. the alkali metal inherently present in the alkali silicate.

In some embodiments, the metal is present in the formulation in an amount of from 100 to 5000 ppm, from 100 to 4000 ppm, e.g. from 100 to 3500 ppm, from 100 to 3000 ppm, from 100 to 2500 ppm, from 100 to 2000 ppm, from 100 to 1500 ppm, from 100 to 1000 ppm, from 100 to 800 ppm, or from 100 to 500 ppm.

In some other embodiments, the metal is present in the formulation in an amount of from 200 to 5000 ppm, from 200 to 4000 ppm, e.g. from 200 to 3500 ppm, from 200 to 3000 ppm, from 200 to 2500 ppm, from 200 to 2000 ppm, from 200 to 1500 ppm, from 200 to 1000 ppm, from 200 to 800 ppm.

In some other embodiments, the metal is present in the formulation in an amount of from 300 to 5000 ppm, from 300 to 4000 ppm, e.g. from 300 to 3500 ppm, from 300 to 3000 ppm, from 300 to 2500 ppm, from 300 to 2000 ppm, from 300 to 1500 ppm, from 300 to 1000 ppm, from 300 to 800 ppm.

In some other embodiments, the metal is present in the formulation in an amount of from 400 to 5000 ppm, from 400 to 4000 ppm, e.g. from 400 to 3500 ppm, from 400 to 3000 ppm, from 400 to 2500 ppm, from 400 to 2000 ppm, from 400 to 1500 ppm, from 400 to 1000 ppm, from 400 to 800 ppm.

In some other embodiments, the metal is present in the formulation in an amount of from 500 to 5000 ppm, from 500 to 4000 ppm, e.g. from 500 to 3500 ppm, from 500 to 3000 ppm, from 500 to 2500 ppm, from 500 to 2000 ppm, from 500 to 1500 ppm, from 500 to 1000 ppm, or from 500 to 800 ppm.

In some of these embodiments, the formulation according to the invention contains sodium silicate having a $SiO_2/Na_2O$ molar ratio of about 6:1 to about 2:1, e.g. of about 5:1 to about 2:1, such as about 4.5:1 to about 2.5:1, in an amount corresponding to a $SiO_2$ concentration of about 1% by weight to about 30% by weight, or about 2% by weight to about 25% by weight, or about 3% to about 20% by weight, or about 4% to about 15%, based on the total weight of the formulation.

In some embodiments, the formulation according to the invention contains potassium silicate having a $SiO_2/K_2O$ molar ratio of about 25:1 to about 2:1, e.g. about 10:1 to about 2:1, or about 5:1 to about 2:1, in an amount corresponding to a $SiO_2$ concentration of about 1% by weight to about 30% by weight, or about 2% by weight to about 25% by weight, or about 3% to about 20% by weight, or about 4% to about 15%, based on the total weight of the formulation.

In some embodiments, the formulation according to the invention contains lithium silicate in a $SiO_2/Li_2O$ molar ratio of about 25:1 to about 2:1, e.g. about 10:1 to about 2:1, or about 5:1 to about 2:1, in an amount corresponding to a $SiO_2$ concentration of about 1% by weight to about 30% by weight, or about 2% by weight to about 25% by weight, or about 3% to about 20% by weight, or about 4% to about 15%, based on the total weight of the formulation.

For example, in some embodiments, the formulation is a solution containing ions of one or more metals, as defined herein above, and one or more alkali silicates, each alkali silicate having a molar ratio of silicon dioxide to alkali oxide ($SiO_2$:$Me_2O$) of from 25:1 to 2:1, e.g. from 6:1 to 2:1, e.g. from 5:1 to 2:1, or from 4.5:1 to 2:1, e.g. from 4.5:1 to 2.5:1, or from 4.5:1 to 3:1, or from 4:1 to 3:1, wherein the metal(s) is/are present at a concentration of from 10 to 5000 ppm, e.g. from 100 to 5000 ppm, from 200 to 4000 ppm, or from 200 to 3500 ppm, e.g. from 200 to 3000 ppm, or from 200 to 2500 ppm, or from 200 to 2000 ppm, e.g. from 200 to 1500 ppm, by weight of the formulation, and the one or more alkali silicates are present in a total amount corresponding to a concentration of $SiO_2$ of about 1 to about 30%, e.g. about 2 to about 25%, or about 3 to about 20%, or about 4 to about 15%, by weight of the formulation.

In some embodiments, the formulation is a solution containing ions of a metal, as defined herein above, e.g. of a transition metal, and an alkali silicate, selected from lithium silicate, sodium silicate and potassium silicate, having a molar ratio of silicon dioxide to alkali oxide ($SiO_2$:$Me_2O$) of from 25:1 to 2:1, e.g. from 6:1 to 2:1, e.g. from 5:1 to 2:1, or from 4.5:1 to 2:1, e.g. from 4.5:1 to 2.5:1, or from 4.5:1 to 3:1, or from 4:1 to 3:1, wherein the metal is present at a concentration of from 10 to 5000 ppm, e.g. from 100 to 5000 ppm, from 200 to 4000 ppm, or from 200 to 3500 ppm, e.g. from 200 to 3000 ppm, or from 200 to 2500 ppm, or from 200 to 2000 ppm, e.g. from 200 to 1500 ppm, by weight of the formulation, and the alkali silicate is present in a total amount corresponding to a concentration of $SiO_2$ of about 1 to about 30%, e.g. about 2 to about 25%, or about 3 to about 20%, or about 4 to about 15%, by weight of the formulation.

In some embodiments, the formulation is a solution containing from 20 to 5000 ppm, e.g. from 50 to 5000 ppm, from 100 to 4000 ppm, or from 200 to 3500 ppm, e.g. from 300 to 3000 ppm, or from 400 to 2500 ppm, or from 500 to 2000 ppm, e.g. from 600 to 1500 ppm, by weight of the formulation, of metal ion, and an alkali silicate having a molar ratio of silicon dioxide to alkali oxide ($SiO_2$:$Me_2O$) of from 15:1 to 2:1, e.g. from 6:1 to 2:1, e.g. from 5:1 to 2:1, or from 4.5:1 to 2:1, e.g. from 4.5:1 to 2.5:1, or from 4.5:1 to 3:1, or from 4:1 to 3:1, at a concentration corresponding to a concentration of $SiO_2$ of about 1 to about 30%, e.g. about 2 to about 25%, or about 3 to about 20%, or about 4 to about 15%, by weight of the formulation.

In some embodiments, the formulation is a solution containing from 100 to 5000 ppm, or from 200 to 3500 ppm, e.g. from 200 to 3000 ppm, or from 200 to 2500 ppm, or from 200 to 2000 ppm, e.g. from 200 to 1500 ppm by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 5000 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 4000 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 3500 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 2 to about 20%, by weight of the formulation.

In some embodiments, the formulation is a solution containing from 100 from 100 to 3000 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 2500 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 2000 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 1500 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 100 to 1000 ppm, by weight of the formulation of metal ion, and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some embodiments, the formulation is a solution containing from 300 to 5000 ppm, e.g. from 300 to 4000 ppm, or from 400 to 3000 pmm, or from 500 to 2500 ppm, by weight of the formulation, of metal ion and an alkali silicate having a molar ratio of silicon dioxide to alkali oxide ($SiO_2$:$Me_2O$) of from 5:1 to 2:1, at a concentration corresponding to a concentration of $SiO_2$ of about 1 to about 30%, by weight of the formulation.

In some of these embodiments, the molar ratio of silicon dioxide to alkali oxide ($SiO_2$:$Me_2O$) is from 4.5:1 to 2:1.

In some further of these embodiments, the molar ratio of silicon dioxide to alkali oxide ($SiO_2$:$Me_2O$) is from 5:1 to 2.5:1.

In some further of these embodiments, the molar ratio of silicon dioxide to alkali oxide ($SiO_2$:$Me_2O$) is from 4.5:1 to 2.5:1.

In some further of these embodiments, the molar ratio of silicon dioxide to alkali oxide ($SiO_2$:$Me_2O$) is from 5:1 to 3:1.

In some further of these embodiments, the molar ratio of silicon dioxide to alkali oxide ($SiO_2$:$Me_2O$) is from 4.5:1 to 3:1.

In some embodiments, the formulation is a mixture of from 100 to 5000 ppm by weight of the formulation of metal ion; and an alkali silicate solution having a molar ratio of silicon dioxide to alkali oxide ($SiO_2$:$Me_2O$) of from 5:1 to 2:1, the alkali silicate being present in an amount corresponding to a $SiO_2$ concentration of about 1% by weight to about 30% by weight, or about 2% by weight to about 25% by weight, or about 3% to about 20% by weight, or about 4% to about 15%, or about 5% to about 10%, based on the total weight of the formulation.

In some embodiments, the formulation contains one or more surfactants, selected from non-ionic, amphoteric (or zwitterionic), anionic surfactants, cationic surfactants, silicon surfactants, fluorinated surfactants, and polymeric surfactants. In some embodiments, the surfactant is nonionic. For example, in some embodiments, the formulation contains from 0.01 to 5% of a surfactant or mixture of surfactants, e.g. from 0.02 to 2%, or from 0.05 to 1%, e.g. from 0.1% to 0.5%, by weight of the formulation.

The formulations according to the present invention are prepared by a mixing a solution of a silicate with a solution comprising metal ions, e.g. transition metals ions or ions of any of the metals mentioned herein above. Due care has to be taken concerning concentration of reactants and products, e.g. using water of good quality, preferably deionized water, observing proper rate of addition and order of addition of the components, working in conservative but realistic temperature ranges and providing sufficient agitation and stirring.

Concentrations of silica used in the various preparations of the present invention vary from one (1) weight % $SiO_2$ or less to undiluted solutions of commercial alkali silicates that could contain 25 weight % $SiO_2$ or more, e.g. from 5% by weight to 20% by weight.

In some embodiments, the formulation is a lithium silicate solution containing metal ions at a concentration of at least 10 ppm, more preferably at least 100 ppm, or at least 200 ppm, and up to 5000 ppm, e.g. up to 4500 ppm, up to 4000 ppm, up to 3500 ppm, up to 3000 ppm, e.g. up to 2500 ppm, up to 2000 ppm, up to 1800 ppm, up to 1500 ppm, up to 1000 ppm, up to 800 ppm, up to 700 ppm, or up to 500 ppm, by total weight of the solution, and lithium silicate having a $SiO_2:Li_2O$ molar ratio of from about 6:1 to about 2:1, e.g. from about 5:1 to about 3:1, from about 4:5 to about 3:1, or from about 4:1 to about 3:1, e.g. from about 3.5:1 to about 3:1, at a concentration of at least 2%, or at least 3%, e.g. at least 4%, or at least 5% and at most 25%, or at most 20%, or at most 18%, or at most 16%, or at most 10%, or at most 8%, by total weight of the solution.

In some embodiments, the formulation is a sodium silicate solution containing metal ions at a concentration of at least 10 ppm, more preferably at least 100 ppm, or at least 200 ppm, and up to 5000 ppm, e.g. up to 4500 ppm, up to 4000 ppm, up to 3500 ppm, up to 3000 ppm, e.g. up to 2500 ppm, up to 2000 ppm, up to 1800 ppm, up to 1500 ppm, up to 1000 ppm, up to 800 ppm, up to 700 ppm, or up to 500 ppm, by total weight of the solution, and sodium silicate having a $SiO_2:Na_2O$ molar ratio of from about 6:1 to about 2:1, e.g. from about 5:1 to about 3:1, from about 4:5 to about 3:1, or from about 4:1 to about 3:1, e.g. from about 3.5:1 to about 3:1, at a concentration of at least 2%, or at least 3%, e.g. at least 4%, or at least 5% and at most 25%, or at most 20%, or at most 18%, or at most 16%, or at most 10%, or at most 8%, by total weight of the solution.

In some embodiments, the formulation is a potassium silicate solution containing metal ions at a concentration of at least 10 ppm, more preferably at least 100 ppm, or at least 200 ppm, and up to 5000 ppm, e.g. up to 4500 ppm, up to 4000 ppm, up to 3500 ppm, up to 3000 ppm, e.g. up to 2500 ppm, up to 2000 ppm, up to 1800 ppm, up to 1500 ppm, up to 1000 ppm, up to 800 ppm, up to 700 ppm, or up to 500 ppm, by total weight of the solution, and potassium silicate having a $SiO_2:K_2O$ molar ratio of from about 6:1 to about 2:1, e.g. from about 5:1 to about 3:1, from about 4:5 to about 3:1, or from about 4:1 to about 3:1, e.g. from about 3.5:1 to about 3:1, at a concentration of at least 2%, or at least 3%, e.g. at least 4%, or at least 5% and at most 25%, or at most 20%, or at most 18%, or at most 16%, or at most 10%, or at most 8%, by total weight of the solution.

The metal ions are cations of any one or more of the metals mention herein. In some embodiments, the metal ions are cations of any one or more metals selected from Zn, Fe, Cu, and Ag; e.g. from Zn, Fe, and Cu; or from Zn and Cu; or from Fe and Cu. In some embodiments, the metal is Zn. In some embodiments, the metal is Fe. In some embodiments, the metal is Cu. In some embodiments, the metal is Ag.

In the solutions defined herein, the silicates and the metal ions selected from Zn, Fe, Cu, and Ag form metal-silicate species that are not considered to be particles, but that may be small metal-containing oligo- and/or polymeric species of a size generally less than 3 nm, e.g. about 2 nm or smaller. These species may be referred to herein as "metal ion-carrying silicate particles".

The Process for Preparing the Metal Containing Silicate Solution

Provided herein is also a process for preparing an aqueous alkali silicate solution containing ions of a metal having an atomic number selected from atomic numbers 21-31, 39-50, 57-82, and 89-93, which comprises admixing a aqueous solution of the silicate and an aqueous solution of a water soluble salt of said metal. A surprising feature of the process described herein resides in the fact that the process does not involve the use of a complexing or chelating agent. Thus, in the process of the present invention, the metal as defined herein above does not need to be reacted with a complexing or chelating agent before admixing with the aqueous solution of the silicate. Therefore, preferably, the formulation is prepared with an aqueous solution of a water soluble salt of said metal that is free from a complexing agent for the metal ion; the method of the invention does not comprise reacting the metal cation with a complexing agent.

The Use of the Colloidal Dispersion

The colloidal dispersions provided herein are useful in removing gaseous compounds and/or odorous compounds. The terms "gaseous compound" or "gas" etc refer to any molecule or compound that can exist as a gas or vapor. The terms "odorous compound" or "odor" etc refer to any molecule or compound detectable to the olfactory system, e.g. perceivable by the human sense of smell of at a certain gas phase concentration, the so-called odor threshold. Odorous compounds can exist as a gaseous compound and can also be present in other media such as a liquid, from which they may evaporate. The term "removing" refers to the action of reducing the concentration of the gaseous and/or odorous compound in e.g. a confined space or in vicinity to an object from which a gaseous and/or odorous compound may otherwise be released.

A method for reducing odor as provided herein generally comprises contacting a particle as defined herein, or a colloidal dispersion as defined herein, with an odorous compound. The odorous compound may be selected from compounds such as mercaptans, ammonia, amines, sulfides, disulfides, trisulfides, thiols, ketones, diketones, carboxylic acids, aldehydes, terpenoids etc.

Unless otherwise indicated or apparent from the context, the term "particle" or "nanoparticle" refers to a silica particle as defined herein, to which one or more metal ions have been adsorbed.

Unless otherwise indicate or apparent from the context, the term "colloidal dispersion" as used herein refers to a stable colloidal dispersion of a silica particle as defined herein, to which one or more metal ions have been adsorbed.

Also provided herein is a substrate treated with a colloidal dispersion as provided herein. In one embodiment, the substrate comprises a nonwoven, woven, or paper web; e.g. the substrate may be part of a filtering device, e.g. an air filter, or part of furniture, a wall-paper, a curtain, a wrapper, etc.

In some embodiments, thus, a non-woven or woven fabric is provided, carrying (i) a plurality of particles of silica having a particle size of from 3 nm to 100 nm, said particles having ions of one or more metals selected from copper, silver, zinc and iron adsorbed at the particle surface and/or (ii) a plurality of silicate particles carrying ions of one or more metals selected from copper, silver, zinc and iron.

Thus, some embodiments are comprise bringing a non-woven or woven fabric into contact with (i) a colloidal dispersion of particles of silica having a particle size of from 3 nm to 100 nm, said particles having ions of one or more metals selected from copper, silver, zinc and iron adsorbed at the particle surface, and/or (ii) an aqueous silicate solution containing metal ions selected from ions of copper, silver, zinc and iron.

Some further embodiments comprise a non-woven or woven fabric that has been treated as described herein.

Thus, in some embodiments, the composition of the invention is used to treat textile, in order to provide it with resistance against malodor from sources such as sweat, smoke etc, or to provide it with a deodorization property. For example, a step of impregnation of any textile may be applied in a textile mill setting, such as generally illustrated in FIG. 1. In such a setting, a fabric is fed into an aqueous dispersion containing the silica particles carrying metal ions, as described herein, e.g a bath containing particles of the invention at a concentration of from 0.001% to 10%, or 0.01 to 1%, e.g. 0.1% by weight; or into a aqueous silicate solution as disclosed herein.

The fabric is allowed a contact time with the bath sufficient to thoroughly wet it with the liquid composition. The subsequent steps are those usually applied in the wet treatment of textiles, e.g. mechanical moisture removal, followed by vacuum moisture removal, straightening of the fabric, and drying of the fabric.

In some other embodiments, the composition of the invention may be incorporated into a laundry detergent, e.g. liquid laundry detergents, or into fabric conditioners, such as liquid fabric softeners. For example, a composition (dispersion, solution) of the invention may be included in such a product in an amount of from 5 to 50% by volume, e.g. 5 to 25% by volume, or 5 to 20% by volume, or 10 to 25% by volume, based on the volume of the final product. In addition to the composition of the invention, the detergent or conditioner may contain any conventional ingredient for this type of product.

In some other embodiments, the compostions of the invention also may be included in products for cleaning and removing malodor in e.g. washing machines. For example, a composition (dispersion, solution) of the invention may be included in such a product in an amount of from 5 to 50% by volume, e.g. 5 to 25% by volume, or 5 to 20% by volume, or 10 to 25% by volume In some other embodiments, the composition of the invention is included in a liquid product for removing malodor emanating from liquid phases, such as may be found in sewers, plumings etc. For example, a composition (dispersion, solution) of the invention may be included in such a product in an amount of from 5 to 50% by volume, e.g. 5 to 25% by volume, or 5 to 20% by volume, or 10 to 25% by volume Advantageously, besides the anti-odor properties, treatment of textile with the formulation of the invention may provide the textile with a number of further properties, e.g. one or more properties selected from:

improved wicking, i.e. fabric feels dryer because moisture is wicked away from the body towards the surface of the fabric where it evaporates, improved dry dirt repellency, increased friction between fibers, higher tensile strength and improved resistance to fraying, improved weave structure and seam slippage, crisp dry hand finish, and delustering of the fabrics.

The textile treated according to the invention may be of any type, e.g. it may be intended for use in air filters, upholstery, curtains, etc. or in garments, such as t-shirts, underwear, socks etc.

The amount of the particles present in or on the substrate may vary depending on the nature of the substrate and its intended application. In some embodiments, for example, the dry, solids add-on level is from about 0.001% to about 20%, in some embodiments from about 0.01% to about 10%, and in some embodiments, from about 0.1% to about 4%, by weight. The term "solids add-on level" refers to the value obtained by by subtracting the weight of the untreated substrate from the weight of the treated substrate (after drying), dividing this calculated weight by the weight of the untreated substrate, and then multiplying by 100%.

The colloidal dispersion may be applied to a substrate using any of a variety of well-known application techniques. Suitable techniques for applying the dispersion to a substrate include printing, dipping, spraying, melt extruding, solvent coating, powder coating, and so forth. The application may result in the metal coated silica particles and/or the metal carrying silicate particles being incorporated within the matrix of the substrate and/or coated onto the surface thereof. In some embodiments, the particles are coated onto one or more surfaces of the substrate. When coated onto the substrate, the resulting thickness of the coating may be minimal so that it is almost invisible to the naked eye. In some embodiments, the thickness is less than about 2 μm ($2 \times 10^{-6}$ m), in some embodiments, the thickness is from about 5 nanometers to about 1 μm. In some embodiments, the thickness is from about 10 nanometers to about 500 nanometers, or from about 20 nanometers to about 200 nanometers.

The amount of colloidal dispersion applied to any particular substrate or surface may depend on factors such as the structure of the surface, the material, the absorbing capacity, the location of the substrate etc. For example, an amount of from 0.1 kg/m$^2$ to 10 kg/m$^2$, e.g. from 0.2 kg/m$^2$ to 5 kg/m$^2$, or from 0.5 kg/m$^2$ to 2 kg/m$^2$ of a colloidal dispersion containing from 100 ppm to 1000 ppm by weight of metal ion, from 1% to 10% by weight of silica, and containing particles having a size of e.g. 3 nm to 20 nm.

In some embodiments, the method of the invention comprises applying a colloidal dispersion as provided herein to a wall, textile, wallpaper, glass, a toilet, and/or a countertop, e.g. in a restroom facility, an industrial building, a public building, in a home, in a vehicle, such as a car, a airplane, a train, or any confined space where odor reduction is desired.

In some embodiments, a pad or cloth is provided, to which the composition of the invention has been applied, e.g. by dipping a fabric into a solution of the colloidal dispersion, allowing the fabric to dry, and cutting appropriately sized pieces of the fabric, said pad or cloth having air deodorizing properties. The pad or cloth may be placed in a confined space, such as a room, a cupboard, a refrigerator, a lavatory etc. in order to reduce or eliminate any malodor in the confined space.

In another embodiment, the colloidal dispersion as provided herein is used as an aerosol odor neutralizer/deodorant. The dispersion may be mixed with a propellant for spraying the particles into the air for removal of gases and odorous compounds. However, in some embodiments, no propellant is used, i.e. the colloidal dispersion contains water as only liquid carrier, and e.g. is sprayed into the air by use of a suitable nebulizer.

Therefore, in some embodiments, a spray bottle is provided, containing a colloidal dispersion as disclosed herein, and optionally a propellant, for use in a confined space, such as a restroom, cloakroom, a lavatory, a kitchen, a smoking room, e.g. as an air refresher.

The amount of the colloidal dispersion required to bring into contact with the gaseous phase (e.g. air containing odorous compounds) of a confined space in order to substantially reduce the odor in said space may depend on factors such as the metal used, the contents of metal in the dispersion, the contents of particles in the dispersion, the level of odorous compounds in the space etc. For example, to substantially reduce the contents of odorous compounds in a gaseous phase, it may suffice to spray into said gaseous phase, an amount of about 1 $g/m^3$ to about 1 $kg/m^3$, e.g. about 1 $g/m^3$ to about 500 $g/m^3$, e.g. about 1 $g/m^3$ to about 100 $g/m^3$, or about 1 $g/m^3$ to about 50 $g/m^3$ of a colloidal dispersion as disclosed herein.

In some embodiments a liquid composition for producing a surface coating is provided, the composition comprising particles of silica having a particle size of from 3 nm to 100 nm, said particles having ions of one or more metals selected from copper, silver, zinc and iron adsorbed at the particle surface; and a liquid carrier for the particles.

In some embodiments a liquid composition for producing a surface coating is provided, the composition comprising particles of silica having a particle size of from 3 nm to 100 nm, said particles having ions of one or more metals selected from copper, silver, zinc and iron adsorbed at the particle surface; and a liquid carrier for the particles.

In some embodiments a liquid composition for producing a surface coating is provided, the composition comprising silicate particles, e.g. silicate particles having a particle size of less than 3 nm or less than 2 nm, said particles carrying ions of one or more metals selected from copper, silver, zinc and iron at the particle surface; and a liquid carrier for the particles The liquid carrier e.g. may comprise solvents and resins of the type used in conventional paints. For examples, the solvent may comprise mineral spirits, aromatic solvents, alcohols, esters, and ketones, or water. The resins may be selected from natural resins, such as lin-seed, coconut, and soybean oil, and synthetic resins, such as alkyds, acrylics, epoxies, and polyurethanes.

In some embodiments, particles of the invention are included in a paint, latex, adhesive, etc. or other liquid formulation to be applied as a surface coating or as an impregnation, varnish, a lacquer etc.

Thus, in some embodiments, the colloidal dispersion of the invention is used as a paint additive, to provide a paint having anti-odor properties. For example, in some embodiments, a paint is provided suitable for use to paint a surface, e.g. wall, ceiling, floor, or surface of an appliance, etc. in a confined space such as a garbage room, a public toilet, a restaurant kitchen, a storage room, a greenhouse, etc.

In some embodiments, therefore, a paint formulation is provided that, in addition to conventional ingredients (e.g. pigment, resin, solvent) contains particles of the present invention. Such a paint formulation may be obtained by admixing a colloidal dispersion of the present invention with a conventional paint formulation, e.g. 50 ml to 500 ml, or 100 ml to 450 ml, or 150 ml to 400 ml, or 200 to 300 ml, of a colloidal dispersion as described herein may be admixed with a conventional paint formulation to obtain a final volume 1 liter of anti-odor paint formulation.

It should be understood that "particles of the present invention" are either silica particles having a particle size of from 3 nm to 100 nm, said particles having ions of one or more metals selected from copper, silver, zinc and iron adsorbed at the particle surface, or the small species (less than 3 nm) formed in an aqueous silicate solution containing metal ions selected from ions of copper, silver, zinc and iron, i.e. the silicate particles carrying said metal ions, as mentioned herein above. In some embodiments, the particles used are the silica particles having a particle size of from 3 nm to 100 nm, said particles having ions of one or more metals selected from copper, silver, zinc and iron adsorbed at the particle surface. In some other embodiments, the particles used are the small silicate particles carrying one or more metal ions selected from copper, silver, zinc and iron.

In addition to the colloidal dispersion of the invention, the anti-odor paint may contain any conventional ingredient, e.g. a binder such as a synthetic resin; a carrier, such as water or an organic solvent; a pigment; and any further additives e.g. fungicidal agents, UV screens, anti-rust agents, etc. The paint may be of emulsion (latex) type, i.e. having water as a carrier, or may be an oil-based paint.

It is considered that when using the colloidal dispersion of the invention e.g. for painting a wall, it may suffice to apply the colloidal dispersion only in the top coat, in combination with conventional paints in underlying coats. In some embodiments, the colloidal dispersion is applied also in one or more of the underlying layers. Thus, in some embodiments, e.g. when treating a wall or other surface previously damaged by e.g. smoke or mildew attack, treatment may comprise first applying a colloidal dispersion of the invention as a a primer coating, followed by applying barrier coating, containing the colloidal dispersion of the invention mixed with a conventional barrier paint, and finally, a top coat containing the colloidal dispersion of the invention mixed with a conventional paint formulation.

For example, in some embodiments, a colloidal dispersion as described herein is applied as a surface primer; followed by an anti-odor barrier paint formulation comprised of from 5-50% by volume of the colloidal dispersion of the invention, e.g. 10-40% by volume, or 20-30% by volume, in any conventional barrier paint formulation, and finally an anti-odor top coat comprised of from 5-50% by volume of the colloidal dispersion of the invention, e.g. 10-40% by volume, or 20-30% by volume, in any conventional paint formulation.

The colloidal dispersion used e.g. may be one containing 5% $SiO_2$ and 100-500 ppm, or 200-400 ppm, of a metal ion as defined herein, e.g. 5% $SiO_2$ and 300 ppm $Cu^{2+}$.

In some embodiments, the anti-odor paint may be a ready-to-use mix containing the particles of the present invention. However, it also is contemplated that a colloidal dispersion of the invention may be provided separately and admixed with a conventional paint before application of the paint.

In some embodiments of the invention, a method for treatment of a surface comprises applying a surface coating to the surface, e.g. a paint, varnish, laquer, adhesive, or any type of solvent-resin mixture, to a surface, optionally allowing the coating to dry a least partially, and applying nanoparticles of the invention to the optionally partly dried surface, e.g. by spraying or brushing.

For example, in some embodiments, a surface coating is applied to a wall, a ceiling or a floor, e.g. by applying a conventional paint formulation, and particles of the invention, e.g. in the form of a colloidal dispersion in a liquid carrier such as water, are applied to the wet paint surface, e.g. by spraying, whereafter the surface is allowed to dry.

The particles of the invention may be applied to a surface at a surface concentration of e.g. about 0.01 to 5 kg/m$^2$; e.g. 0.1 to 3 kg/m$^2$; e.g. 0.5 to 2 kg/m$^2$. For example, in some embodiments, a colloidal dispersion of the invention is used, containing about 100 to about 1000 ppm of a metal as mentioned herein, and about 1 to about 20% $SiO_2$, wherein the particles have a size of from about 3 to about 50 nm, e.g. from about 3 to about 10 nm, or about 5 nm. The particles of the invention may be applied to a surface at a surface concentration of e.g. about 0.01 to 5 kg/m$^2$; e.g. 0.1 to 3 kg/m$^2$; e.g. 0.5 to 2 kg/m$^2$.

In some further embodiments, a colloidal dispersion of the invention is used, containing about 100 to about 500 ppm of a metal as mentioned herein, and about 3 to about 10% $SiO_2$, wherein the particles have a size of from about 3 to about 10 nm.

In some of the above embodiments, the colloidal dispersion contains copper as a metal. In some other particular embodiments, the colloidal dispersion contains zinc as a metal. In still other embodiments, the colloidal dispersion contains iron as a metal.

In some embodiments, a method is provided for the treatment of woven or non-woven material, e.g. a fabric such as cotton, wool, or any synthetic fabric, by bringing the material into contact with metal coated silica particles, e.g. in the form of a colloidal dispersion. The material may be dipped into a liquid formulation containing the particles in a liquid carrier, such as water optionally containing a surfactant, and allowed to dry. Therefore, in some embodiments, a woven or non-woven material is provided, with improved anti-odor properties. Such a material may be present e.g. in clothes, such as sport garments, underwear, socks, trousers, t-shirts, overalls, etc; in footwear, such as sport shoes, boots etc; in insoles for footwear; and in fabrics for interior decoration, such a curtains, or upholstery fabrics.

In some embodiments, therefore, a non-woven or woven material is provided, which carries at its surface a plurality of metal coated silica particles of the invention.

In some embodiments, an object is provided, e.g. selected from a garment, such as a sport garment, underwear, a sock, a trouser, a t-shirt, an overall, etc; footwear, such as sport shoes, boots etc; an insole for a shoe or a boot; or an interior decoration object, such as a curtain, a sofa cover, a mattress cover, a pillowcase, etc. comprising a non-woven or woven material that has been treated as mentioned herein above, i.e. which carries a plurality of the metal coated particles disclosed herein.

Herein below, examples of metal coated silica particles and colloidal dispersions thereof, which may be used in embodiments of the method of the invention, are described. Useful silver coated silica particles, colloidal dispersions thereof, and methods for their preparation are described in WO 2011/037523.

In the examples, stock solutions containing 9000 ppm of salts of some representative metals according to the invention were used, as shown in Table 2.

TABLE 2

| Stock solutions containing 9000 ppm of metal | | | | |
|---|---|---|---|---|
| Metal | Salt | Molar weight (g) | pH | Appearance/ comments |
| Cu | $CuCl_2 \cdot 2H_2O$ | 170.48 | 4.1 | Clear, blue |
| Fe | $FeCl_3 \cdot 6H_2O$ | 270.30 | 1.6 | Clear, orange |
| Zn | $C_4H_6O_4Zn \cdot 2H_2O$ | 219.51 | 5.8 | Some sediment. Clear supernatant |

EXAMPLES

Examples of colloidal dispersions that are useful in the method of the invention were prepared using various metal solutions in admixture with different silica sols, of which some had aluminosilicate sites at the particle surface. The silica sols used were of the Bindzil® series, sold by Akzo Nobel AB. Characteristics of silica sols used in the examples are shown in Table 3.

TABLE 3

| | Characterization of Bindzil® silica sols | | | | | | | |
|---|---|---|---|---|---|---|---|---|
| Bindzil® | Specific surface area m$^2$/g | Part. size nm | Silica % | pH | Viscosity cp | Density | $Na_2O$ % by weight | $Al_2O_3$ % by weight |
| 15/500 | 525 | 5 | 15 | 10.0 | 3 | 1.1 | 0.4 | — |
| 159/500 | 525 | 5 | 15 | 9.5 | 3.5 | 1.1 | 0.4 | 0.5 |
| 30/360 | 360 | 7 | 30 | 10.1 | 6 | 1.2 | 0.6 | — |
| 257/360 | 360 | 7 | 25 | 10.0 | 4 | 1.2 | 0.6 | 0.4 |
| 30/220 | 220 | 12 | 30 | 9.9 | 5 | 1.2 | 0.31 | — |
| 309/220 | 220 | 12 | 30 | 10.5 | <15 | 1.2 | 0.53 | 0.42 |
| 40/130 | 130 | 22 | 40 | 9.1 | 8 | 1.3 | 0.2 | — |

In the examples, 50 g of a silica sol containing 5% by weight of $SiO_2$ were added in a thin stream to 20 g of the dilute solution of metal salt under vigorous agitation. This is the preferred order of addition of the components of the compositions of the present invention but the components can also be added in the reverse order (i.e. a dilute solution of the metal salt is added to the silica sol). When this has been done, this is indicated by a star (*).

The composite sols were prepared by mixing 20 g of metal salt solutions containing 90, 270, 450, 1000, 2000, 3000, or 4000 ppm metal, prepared from the stock solutions of Table 2, with 50 g of silica sol diluted with deionized water to 5% by weight of $SiO_2$. The metal concentration of the composite sols thus was 2/7 of that of the original metal salt solutions, viz. 26, 77, 129, 286, 571, 857 and 1142 ppm metal, respectively, whereas the silica concentration was 5/7 of that of the original silica sol, viz. 3.6% by weight.

The below tables show some features of colloidal dispersions obtained when mixing solutions of salts of $Cu^{2+}$, $Fe^{3+}$, and $Zn^{2+}$ with different types of silica sol. Features of silver containing colloidal dispersions may be found in WO 2011/037523.

In column 4, the amounts of 1 M NaOH solution needed to raise the pH to between 10.0 and 11.0 are shown. In most cases alkali was added to the mixture of silica sol and metal solution, but in some cases it was added to the diluted silica sol before the sol was mixed with the salt solution or the metal salt solution was mixed with the sol.

TABLE 4

Cu sol of Bindzil® 159/500 with different concentrations of $Cu^{2+}$

| Ex. | Conc. ppm | pH before adjustment | Number of drops of 1M NaOH | pH after adjustment | Appearance/comments | $C_s^{(1)}$ atoms/nm² |
|---|---|---|---|---|---|---|
| 1 | 26 | 10.1 | 5 | 10.5 | Clear/colorless | 0.013 |
| 2 | 77 | 9.7 | 8 | 10.5 | Clear/colorless | 0.039 |
| 3 | 129 | 9.2 | 10 | 10.5 | Clear/colorless | 0.069 |
| 4 | 286 | 6.8 | 18 | 10.5 | Clear/faint blue | 0.150 |
| 5 | 571 | 5.4 | 54 | 10.5 | Clear/blue | 0.300 |
| 6 | 1286 | 5.4 | 70 | 10.5 | First blue gel. Cleared to faintly hazy liquid in 3-5 days | 0.675 |
| 7* | 1286 | 5.6 | 72 | 10.5 | First blue gel. Cleared to faintly hazy liquid in 3-5 days | 0.675 |

(1)Calculated according to Equation 1, cf. below.

TABLE 5

Cu sol of Bindzil® 15/500 with different concentrations of $Cu^{2+}$

| Ex. | Conc. ppm | pH before adjustment | # drops of 1M NaOH | pH after adjustment | Appearance/comments |
|---|---|---|---|---|---|
| 1 | 26 | 10.3 | 4 | 10.5 | Clear/colorless |
| 2 | 77 | 10.0 | 6 | 10.5 | Clear/colorless |
| 3 | 129 | 9.8 | 10 | 10.5 | Clear/colorless |
| 4 | 286 | 9.0 | 20 | 10.5 | Clear/faint blue |
| 5* | 286 | 8.9 | 21 | 10.5 | Clear/blue |
| 6 | 571 | 6.0 | 64 | 10.5 | First blue gel. After 10 days, blue hazy liquid |
| 7* | 571 | 6.0 | 44 | 10.5 | First blue gel. After 10 days, blue hazy liquid |

TABLE 6

Fe sol of Bindzil® 159/500 with different concentrations of $Fe^{3+}$

| Ex. | Conc. ppm | pH before adjustment | # drops of 1M NaOH | pH after adjustment | Appearance/comments |
|---|---|---|---|---|---|
| 1 | 26 | 9.7 | 10 | 10.4 | Faint haze |
| 2 | 77 | 8.0 | 10 | 10.5 | Clear/yellow |
| 3 | 129 | 6.4 | 12 | 12 | Clear/yellow |
| 4 | 286 | 5.1 | 33 | 10.5 | Clear/yellow |
| 5 | 571 | 3.2 | 0 | — | Milky, viscous, sediment after 24 h |
| 6* | 571 | 3.2 | 0 | — | Milky, viscous, sediment after 24 h |

TABLE 7

Fe sol of Bindzil® 15/500 with different concentrations of $Fe^{3+}$

| Ex. | Conc. ppm | pH before adjustment | Number of drops of 1M NaOH | pH after adjustment | Appearance/comments |
|---|---|---|---|---|---|
| 1 | 26 | 10.3 | 0 | 10.3 | Clear |
| 2 | 77 | 9.9 | 9 | 10.5 | Clear |
| 3 | 129 | 9.4 | 15 | 10.5 | Faint haze |
| 4 | 286 | 7.2 | 35 | 10.5 | Hazy |
| 5* | 286 | 7.1 | 29 | 10.5 | Faint haze |
| 6 | 571 | 3.1 | 48 | 10.5 | Gel/orange |

TABLE 8

Zn sol of Bindzil® 159/500 with different concentrations of $Zn^{2+}$

| Ex. | Conc. ppm | pH before adjustment | # drops of 1M NaOH | pH after adjustment | Appearance/comments |
|---|---|---|---|---|---|
| 1 | 26 | 9.3 | 16 | 10.5 | Clear |
| 2 | 77 | 9.8 | 14 | 10.7 | Clear |
| 3 | 129 | 9.0 | 20 | 10.7 | Clear |
| 4 | 286 | 9.9 | 22 | 10.5 | Clear |
| 5 | 571 | 7.7 | 50 | 10.6 | Clear |

TABLE 9

Zn sol of Bindzil ® 15/500 with different concentrations of $Zn^{2+}$

| Ex. | Conc. ppm | pH before adjustment | # drops of 1M NaOH | pH after adjustment | Appearance/ comments |
|---|---|---|---|---|---|
| 1 | 26 | 10.1 | 14 | 10.5 | Clear |
| 2 | 77 | 9.9 | 14 | 10.5 | Clear |
| 3 | 129 | 9.8 | 18 | 10.5 | Clear |
| 4 | 286 | 9.2 | 27 | 10.5 | Clear |
| 5 | 571 | 7.4 | 50 | 10.6 | Faint haze |

The examples in the below Table 10 show that for a given concentration of metal, for instance 500 ppm Cu and Zn, stable composite sols of different concentrations of 5 nm silica particles can be prepared. The compositions of Table 10 were made by mixing the diluted silica sol into the transition metal solution and then raising the pH of the solution to pH 10 by the dropwise addition of 1 M NaOH.

TABLE 10

Compositions containing 500 ppm Cu or Zn and aluminized 5 nm particles (Bindzil ® 159/500) of varying silica concentration

| Metal | Ex. | Silica conc. % | Comments |
|---|---|---|---|
| Cu | 1 | 5 | Clear |
|  | 2 | 10 | Clear |
|  | 3 | 15 | Clear/faint haze[1] |
| Zn | 4 | 5 | Clear |
|  | 5 | 10 | Clear |
|  | 6 | 15 | Clear/faint haze[1] |

[1]From silica sol

Different composite sols of the invention were prepared containing 500 ppm $Zn^{2+}$ in combination with silica sols of different particle sizes and silica concentrations. In each case, a stable sol was obtained. The faint haze, observed in examples 2 and 3, was due the silica sol and was observable already before admixing the sol with the metal.

The sols prepared were as shown in Table 11.

TABLE 11

Compositions containing 500 ppm Zn and silica sols of varying sizes and types

| Example | Particle size (nm) | Silica conc. % | Bindzil ® type | Comments |
|---|---|---|---|---|
| 1 | 5 | 15 | 159/500 | Clear |
| 2 | 7 | 10 | 257/360 | Faint haze[1] |
| 3 | 12 | 5 | 309/220 | Faint haze[1] |

[1]From silica sol

Table 12 shows some further examples of the invention, having metal ion concentrations as high as 2000 ppm, corresponding to 31 mM in the case of Zn.

TABLE 12

Formulations of Bindzil ® 159/500 and 2000 ppm of Zn and a silica concentration of 3.6% by weight

| Metal | pH before adjustment | Appearance before pH adjustment | Number of drops of 1M NaOH | pH after adjustment | Appearance after pH adjustment |
|---|---|---|---|---|---|
| Zn | 8.4 | Clear liquid | 75 | 10.6 | Clear liquid |

Examples of Different Metal Ions Adsorbed on the Particle Surface.

Table 13 shows stable formulations of 5 nm silica particles and aqueous solutions containing two or more metal ions. The formulations were made by adding 50 g of silica sol, diluted to desired concentration of silica, to 20 g of an aqueous solution containing two or more kinds of metal ions under vigorous stirring.

With more two or more different metals, equation (1) can be used to calculate the surface concentration of each metal, $C_{s1}$ and $C_{s2}$, and the total surface concentration of metals, $C_{stot}$:

$$C_{s1}=60M_1/(M_{met1}AK)=(60/AK)(M_1/M_{met1})$$

$$C_{s2}=60M_2/(M_{met2}AK)=(60/AK)(M_2/M_{met2})$$

$$C_{stot}=C_{s1}+C_{s2}=(60/AK)[M_1/M_{met1}+M_2/M_{met2}].$$

TABLE 13

Stable formulations of silica particles from Bindzil ® 159/500, Bindzil ® 257/360 and Bindzil ® 309/220 and two types of metal ions with total concentration of 286 ppm and silica contration of 3.6% by weight.

| Combinations | Ex. | Metal weight ratio | Sol type | $C_{s, met1}$ atoms per $nm^2$ | $C_{s, met2}$ atoms per $nm^2$ | $C_{s, tot}$ atoms per $nm^2$ | Comments |
|---|---|---|---|---|---|---|---|
| Cu + Gd | 1 | 2:1 | 159/500 | 0.100 | 0.020 | 0.120 | Clear |
|  | 2 | 1:1 | 159/500 | 0.075 | 0.030 | 0.105 | Clear |
|  | 3 | 1:2 | 159/500 | 0.050 | 0.040 | 0.090 | Clear |
|  | 4 | 2:1 | 257/360 | 0.139 | 0.028 | 0.167 | Clear |
|  | 5 | 2:1 | 309/220 | 0.227 | 0.046 | 0.273 | Clear |
| Cu + Sn | 6 | 2:1 | 159/500 | 0.100 | 0.027 | 0.127 | Clear |
|  | 7 | 1:1 | 159/500 | 0.075 | 0.040 | 0.115 | Some haze |
|  | 8 | 1:2 | 159/500 | 0.050 | 0.054 | 0.104 | Some haze |

With three different metals equation (1) can be used to calculate the surface concentration of each metal, $C_{s1}$, $C_{s2}$ and $C_{s3}$, and the total surface concentration of metals, $C_{stot}$ $C_{s1} = 60M_1/(M_{met1}AK) = (60/AK)(M_1/M_{met1})$ $C_{s2} = 60M_2/(M_{met2}AK) = (60/AK)(M_2/M_{met2})$ $C_{s3} = 60M_3/(M_{met3}AK) = (60/AK)(M_3/M_{met3})$ $C_{stot} = C_{s1} + C_{s2} + C_{s3} = (60/AK)[M_1/M_{met1} + M_2/M_{met2} + M_3/M_{met3}]$

TABLE 14

Stable formulations of silica particles from Bindzil® 159/500, Bindzil® 257/360, Bindzil® 309/220 and Bindzil® 40/130 and three types of metal ions with total concentration of 286 ppm and silica contration of 3.6% by weight

| Metals | Metal weight ratio | Bindzil® type | $C_{s, met1}$ atoms per nm² | $C_{s, met2}$ atoms per nm² | $C_{s, met3}$ atoms per nm² | $C_{s, tot}$ atoms per nm² | Comments |
|---|---|---|---|---|---|---|---|
| Cu + Sn + Co | 1:1:1 | 159/500 | 0.050 | 0.027 | 0.054 | 0.131 | Clear |
| | | 257/360 | 0.069 | 0.037 | 0.074 | 0.180 | Clear |
| | | 309/220 | 0.114 | 0.061 | 0.123 | 0.298 | Haze[1] |
| | | 40/130 | 0.192 | 0.103 | 0.207 | 0.502 | Haze[1] |

[1] From silica sol

Mono-metal sols can be blended to give sol mixtures containing particles with a single metal, but different metals, adsorbed on the particles, as is shown in Table 15.

TABLE 15

Mixtures of copper and gadolinium sols and copper and zinc sols of various ratios. Each sol contains 286 ppm metal before mixing

| Metal sol mixture | Metal sol ratio | pH | Comments |
|---|---|---|---|
| ex. 4, table 4, copper sol + | 2:1 | 9.9 | Clear, colorless |
| ex. 4, table 8, zinc sol | 1:1 | 9.9 | Clear, colorless |
| | 1:2 | 9.9 | Clear, colorless |

Examples Showing Z-Potential of the Composite Sols of the Invention

The Z-potentials of different copper or zinc containing sols were measured, at the pH and concentrations at which they were prepared, cf. Tables 4, 5, and 10. As a comparison, the Z-potentials of some silica sols were measured. The results are shown in Tables 16 and 17.

TABLE 16

Zeta potential measured in various composite sols of the invention

| Sample | Example | Metal conc. ppm | $C_{s,met1}$ atoms per nm² | Zeta potential mV |
|---|---|---|---|---|
| 1 | #1, Table 4 | Cu, 26 | 0.014 | −55.0 |
| 2 | #3, Table 4 | Cu, 129 | 0.067 | −47.0 |
| 3 | #5, Table 4 | Cu, 571 | 0.300 | −54.9 |
| 4 | #6, Table 5 | Cu, 571 | 0.300 | −50.1 |
| 5 | #6, Table 4 | Cu, 1286 | 0.675 | −46.1 |
| 6 | #1, Table 11 | Zn, 500 | 0.061 | −36.7 |
| 7 | #2, Table 11 | Zn, 500 | 0.127 | −43.2 |
| 8 | #3, Table 11 | Zn, 500 | 0.417 | −45.4 |
| 9 | #3, Table 10 | Cu, 500 | 0.063 | −45.1 |

TABLE 17

Zeta potential measured in silica sols

| Sample | Silica sol | Zeta potential mV |
|---|---|---|
| 1 | Bindzil® 15/500 | −49.3 |
| 2 | Bindzil® 159/500 | −46.8 |
| 3 | Bindzil® 159/50, 10% SiO₂ | −56.1 |
| 4 | Bindzil® 159/50, 15% SiO₂ | −45.1 |

TABLE 17-continued

Zeta potential measured in silica sols

| Sample | Silica sol | Zeta potential mV |
|---|---|---|
| 5 | Bindzil® 257/360, 10% SiO₂ | −44.1 |
| 6 | Bindzil® 309/220, 15% SiO₂ | −45.3 |
| 7 | Bindzil® 40/130 | −32.8 |

The absolute values of the Z-potentials of the composite sols of the invention are remarkably high even at the highest metal concentration, 1286 ppm, which indicates high stability towards flocculation or gelling.

Metal containing silicate solutions were prepared by use of either commercially available alkali silicate solutions, e.g. alkali silicate solutions having a $SiO_2:Me_2O$ molar ratio of 3.3, or of alkali silicate solutions prepared as follows:

4.3 Ratio, 15% by Weight SiO₂, Na Silicate Solution.

1 part of a 7 nm silica sol, Bindzil®30/360, diluted to 9.6 weight % SiO₂, was mixed with 2 parts of 3.3 molar ratio sodium silicate diluted to 17.6 weight % SiO₂, under magnetic stirring. The milky white dispersion of silica gel was heated to 96° C. under magnetic stirring over a period of 60 minutes. At about 85° C. the dispersion started to become clear. At 96° C., after 60 minutes, the dispersion was water clear and the heater was turned off. The pH was 11.6 at 20° C.

4.3 Ratio, 15% by Weight SiO₂, K Silicate Solution.

1 part of 7 nm silica sol, Bindzil® 30/360, diluted to 10.7 weight % SiO₂, was mixed with 2.31 parts of 3.3 molar ratio potassium silicate diluted to 16.8 weight % SiO₂ under magnetic stirring. The dispersion was heated to 96° C. under magnetic stirring over a period of 60 minutes when the heater was turned off. The pH was 11.6 at 20° C.

4.3 Ratio, 15% by Weight SiO₂, Li Silicate Solution.

220 g Bindzil® 30/360 decationized with a strong cation exchange resin in the hydrogen form, pH 2,0, were mixed with 204 g 2 M LiOH (pH 13.1) under stirring by a magnet bar at 20° C. The stirring was continued and after 12 hours the opaque watery gel had cleared and thinned to a water clear solution of pH 11.2.

2.5 Ratio 24.1% $SiO_2$ Na Silicate Solution

A solution of 2.5 $SiO_2$:$Na_2O$ molar ratio sodium silicate was prepared by adding 7.23 g NaOH dissolved in 15 g deionized water (8.14 M NaOH) to 180 g of 3.3 $SiO_2$:$Na_2O$ molar ratio, 27.0% $SiO_2$, sodium silicate solution under stirring by a magnet bar. The mixture was heated to 96° C. over a period of 4 hours, and was kept at 96° C. for 30 minutes. The heater was turned off and the mixture was allowed to cool to room temperature under moderate agitation over night. The solution contained 24.1% $SiO_2$, and had a pH of 12.3.

Alkali silicate solutions: 3.3 molar ratio Na silicate ("Na 3.3"), 10% $SiO_2$, 2.5 molar ratio Na silicate ("Na 2.5"), 10% $SiO_2$, 3.3 molar ratio K silicate ("K 3.3"), 10% $SiO_2$ and 3.3 molar ratio Li silicate ("Li 3.3"), 10% $SiO_2$.

Solution 1

An aqueous solution containing 1000 ppm by weight of $Zn^{2+}$ was prepared by dissolving 0.208 g $ZnCl_2$ in sufficient deionized water to obtain 100 g of $Zn^{2+}$ solution. Under vigorous stirring using a bar magnet, 5 g of the $Zn^{2+}$ solution was added to 5 g of a solution of 3.3 $SiO_2$:$Li_2O$ molar ratio lithium silicate containing 10% $SiO_2$, to obtain Solution 1.1. The appearance of the formulation was observed at the end of the admixing.

Solutions 2 to 5

Solutions 2 to 4 were prepared following the same general procedure as in Solution 1, using different metal salts and the 3.3 molar ratio lithium silicate, at varying amounts of metal and silicate. For each formulation the appearance was noted after admixing.

Details of the formulations and the results are shown in Tables 18 to 22.

TABLE 18

Mixtures of 3.3 molar ratio Li silicate ("Li 3.3") solutions with $ZnCl_2$ solutions

| Sol. | Formulation | $SiO_2$ % | Metal ppm | Ratio silicate soln. to metal soln. | Appearance |
|---|---|---|---|---|---|
| 1.1 | Li 3.3 20% + Zn 3000 ppm[1] | 10 | 1500 | 1:1 | Clear/colourless |
| 1.2 | Li 3.3 20% + Zn 3000 ppm | 6.7 | 2000 | 1:2 | Slight precipitation |
| 1.3 | Li 3.3 20% + Zn 3000 ppm | 5 | 2250 | 1:3 | Precipitation |
| 1.4 | Li 3.3 20% + Zn 3000 ppm | 13.3 | 1000 | 2:1 | Clear/colourless |
| 1.5 | Li 3.3 10% + Zn 3000 ppm | 5 | 1500 | 1:1 | Slight haze |
| 1.6 | Li 3.3 10% + Zn 3000 ppm | 3.3 | 2000 | 1:2 | Slight precipitation |

[1]pH of a 3000 ppm $ZnCl_2$ solution is 6.3

TABLE 19

Mixtures of 3.3 molar ratio Li silicate ("Li 3.3") solutions with $FeCl_3$ solutions

| Sol. | Formulation | $SiO_2$ % | Metal Ppm | Ratio silicate soln. to metal soln. | Appearance |
|---|---|---|---|---|---|
| 2.1 | Li 3.3 20% + Fe 3000 ppm[1] | 13.3 | 1000 | 2:1 | Gel/sludge |
| 2.2 | Li 3.3 20% + Fe 3000 ppm[1] | 10 | 1500 | 1:1 | Gel/sludge |
| 2.3 | Li 3.3 10% + Fe 3000 ppm | 5 | 1500 | 1:1 | Gel/sludge |

TABLE 19-continued

Mixtures of 3.3 molar ratio Li silicate ("Li 3.3") solutions with $FeCl_3$ solutions

| Sol. | Formulation | $SiO_2$ % | Metal Ppm | Ratio silicate soln. to metal soln. | Appearance |
|---|---|---|---|---|---|
| 2.4 | Li 3.3 10% + Fe 3000 ppm | 7.5 | 750 | 3:1 | Gel/sludge |
| 2.5 | Li 3.3 10% + Fe 1000 ppm | 5 | 500 | 1:1 | Clear/yellow |
| 2.6 | Li 3.3 10% + Fe 1000 ppm | 2.5 | 750 | 1:3 | Slight haze |

[1]pH of a 3000 ppm $FeCl_3$ solution is 2.

TABLE 20

Mixtures of 3.3 molar ratio Li silicate ("Li 3.3") solutions with $CuSO_4$ solutions

| Sol. | Formulation | $SiO_2$ % | Metal ppm | Ratio silicate soln. to metal soln. | Appearance |
|---|---|---|---|---|---|
| 3.1 | Li 3.3 10% + Cu 3000 ppm | 5 | 1500 | 1:1 | Turbid, precipitation |
| 3.2 | Li 3.3 10% + Cu 3000 ppm | 8 | 600 | 4:1 | Slight haze, blue |
| 3.3 | Li 3.3 10% + Cu 1000 ppm | 5 | 500 | 1:1 | Clear, blue |

[1]pH of 3000 ppm $CuSO_4$ solution is 4.6

TABLE 21

Mixtures of 3.3 molar ratio Li silicate solutions with $AgNO_3$ solutions

| Sol. | Formulation | $SiO_2$ % | Metal ppm | Ratio silicate soln. to metal soln. | Appearance |
|---|---|---|---|---|---|
| 4.1 | Li 3.3 20% + Ag 3000 ppm | 10 | 1500 | 1:1 | Clear, colorless |
| 4.2 | Li 3.3 20% + Ag 3000 ppm | 13 | 1000 | 2:1 | Clear, colorless |
| 4.3 | Li 3.3 20% + Ag 3000 ppm | 15 | 750 | 3:1 | Clear, colorless |
| 4.4 | Li 3.3 20% + Ag 3000 ppm | 16 | 600 | 4:1 | Clear, colorless |
| 4.5 | Li 3.3 10% + Ag 1000 ppm | 5 | 500 | 1:1 | Clear, colorless |

[1]pH of 3000 ppm $AgNO_3$ solution is 7.7

TABLE 22

Mixtures of 3.3 molar ratio Li silicate solutions with $FeCl_3$ solutions

| Sol. | Formulation | $SiO_2$ % | Metal ppm | Ratio silicate soln. to metal soln. | Appearance |
|---|---|---|---|---|---|
| 5.1 | Li 3.3 10% + Fe 5143 ppm | 8 | 1029 | 4:1 | Clear/light gray |
| 5.2 | Li 3.3 10% + Fe 3000 ppm | 5 | 1500 | 1:1 | Clear/light gray |
| 5.3 | Li 3.3 10% + Fe 3000 ppm | 2 | 2400 | 1:4 | Clear/colourless |
| 5.4 | L 3.3 10% + Fe 3000 ppm | 8 | 600 | 4:1 | Clear/light gray |

Solution 6

An aqueous solution containing 3000 ppm by weight of $Ag^+$ was prepared by dissolving 0.472 g $AgNO_3$ in sufficient deionized water to obtain 100 g of $Ag^+$ solution. Under vigorous stirring using a bar magnet, 5 g of the $Ag^+$ solution was added to 5 g of a solution of 3.3 $SiO_2:Na_2O$ molar ratio sodium silicate containing 10% $SiO_2$, to obtain Solution 6.1. The appearance of the formulation was observed at the end of the admixing.

Solutions 6.2 to 6.7 were prepared following the same general procedure as used to prepare Solution 6.1, but varying the concentration of either one or both of the solutions and/or the relative amounts of the solutions admixed. For each formulation the appearance was noted after admixing. Details of the formulations and the results are shown in Table 23.

TABLE 23

Mixtures of 3.3 molar ratio Na silicate ("Na 3.3") solutions with $AgNO_3$ solutions

| Sol. | Formulation | $SiO_2$ % | Metal ppm | Ratio silicate soln. to metal soln. | Appearance |
|---|---|---|---|---|---|
| 6.1 | Na 3.3 10% + Ag 3000 ppm | 5 | 1500 | 1:1 | Clear/yellow |
| 6.2 | Na 3.3 10% + Ag 3000 ppm | 3.3 | 2000 | 1:2 | Clear/yellow |
| 6.3 | Na 3.3 15% + Ag 5040 ppm | 7.5 | 2520 | 1:1 | Clear/yellow |
| 6.4 | Na 3.3 15% + Ag 5040 ppm | 5 | 3360 | 1:2 | Clear/yellow |
| 6.5 | Na 3.3 27% + Ag 5040 ppm | 13.5 | 2520 | 1:1 | Clear/colourless |
| 6.6 | Na 3.3 27% + Ag 5040 ppm | 5.4 | 4032 | 1:4 | Clear/yellow |
| 6.7 | Na 3.3 27% + Ag 5040 ppm | 10.8 | 3024 | 2:3 | Clear/yellow |

Solutions 7 to 16

Solutions 7 to 9 (Sol. 7.1 through 9.3) were prepared following the same general procedure as in Solution 6, using different metal salts and the 3.3 molar ratio sodium silicate, at varying amounts of metal and silicate. For each formulation the appearance was noted after admixing. Details of the formulations and the results are shown in Tables 24 to 26.

TABLE 24

Mixtures of 3.3 molar ratio Na silicate ("Na 3.3") solutions with $CuSO_4$ solutions

| Sol. | Formulation | $SiO_2$ % | Metal ppm | Ratio silicate soln. to metal soln. | Appearance |
|---|---|---|---|---|---|
| 7.1 | Na 3.3 10% + Cu 3000 ppm | 5 | 1500 | 1:1 | precipitation |
| 7.2 | Na 3.3 10% + Cu 3000 ppm | 6.7 | 1000 | 2:1 | Clear/blue |
| 7.3 | Na 3.3 10% + Cu 3000 ppm | 8 | 600 | 4:1 | Clear/blue |
| 7.4 | Na 3.3 10% + Cu 1000 ppm | 5 | 500 | 1:1 | Clear/blue |
| 7.5 | Na 3.3 10% + Cu 1000 ppm | 3.3 | 667 | 1:2 | Clear/blue |
| 7.6 | Na 3.3 10% + Cu 3000 ppm | 2 | 800 | 1:4 | Slight haze |

TABLE 25

Mixtures of 3.3 molar ratio Na silicate ("Na 3.3") solutions with $FeCl_3$ solutions

| Sol. | Formulation | $SiO_2$ % | Metal ppm | Ratio silicate soln. to metal soln. | Appearance |
|---|---|---|---|---|---|
| 8.1 | Na 3.3 10% + Fe 3000 ppm | 6.7 | 1000 | 2:1 | sludge |
| 8.2 | Na 3.3 10% + Fe 3000 ppm | 8 | 600 | 4:1 | sludge |
| 8.3 | Na 3.3 10% + Fe 1000 ppm | 5 | 500 | 1:1 | Clear/light yellow |
| 8.4 | Na 3.3 10% + Fe 1000 ppm | 3.3 | 667 | 1:2 | Clear/light yellow |
| 8.5 | Na 3.3 10% + Fe 3000 ppm | 6.7 | 1000 | 2:1 | sludge |
| 8.6 | Na 3.3 10% + Fe 3000 ppm | 8 | 600 | 4:1 | sludge |

TABLE 26

Mixtures of 3.3 molar ratio Na silicate ("Na 3.3") solutions with $FeCl_3$ solutions

| Sol. | Formulation | $SiO_2$ % | Metal ppm | Ratio silicate soln. to metal soln. | Appearance |
|---|---|---|---|---|---|
| 9.1 | Na 3.3 10% + Fe 3000 ppm | 5 | 1500 | 4:1 | Clear/dark gray blue |
| 9.2 | Na 3.3 10% + Fe 3000 ppm | 2 | 2400 | 1:4 | Clear/colorless |
| 9.3 | Na 3.3 10% + Fe 3000 ppm | 8 | 600 | 4:1 | Clear/light gray |

Solution 10

An aqueous solution containing 3000 ppm by weight of $Ag^+$ was prepared by dissolving 0.472 g $AgNO_3$ in sufficient deionized water to obtain 100 g of $Ag^+$ solution. Under vigorous stirring using a bar magnet, 2.5 g of the $Ag^+$ solution was added to 10 g of a solution of 3.3 $SiO_2:K_2O$ molar ratio potassium silicate containing 10% $SiO_2$, to obtain Solution 10.1. The appearance of the formulation was observed at the end of the admixing.

Solutions 10.2 to 10.6 were prepared following the same general procedure as used to prepare Solution 10.1, but varying the concentration of either one or both of the solutions and/or the relative amounts of the solutions admixed. For each formulation the appearance was noted after admixing. Details of the formulations and the results are shown in Table 26.

TABLE 26

Mixtures of 3.3 molar ratio K silicate ("K 3.3") solutions with $AgNO_3$ solutions

| Sol. | Formulation | $SiO_2$ % | Metal ppm | Ratio silicate soln. to metal soln. | Appearance |
|---|---|---|---|---|---|
| 10.1 | K 3.3 20% + Ag 3000 ppm | 16 | 600 | 4:1 | Clear/colourless |
| 10.2 | K 3.3 20% + Ag 3000 ppm | 15 | 750 | 3:1 | Clear/colourless |
| 10.3 | K 3.3 20% + Ag 3000 ppm | 13 | 1000 | 2:1 | Clear/colourless |
| 10.4 | K 3.3 20% + Ag 3000 ppm | 10 | 1500 | 1:1 | Clear/colourless |

TABLE 26-continued

Mixtures of 3.3 molar ratio K silicate ("K 3.3") solutions with AgNO₃ solutions

| Sol. | Formulation | SiO₂ % | Metal ppm | Ratio silicate soln. to metal soln. | Appearance |
|---|---|---|---|---|---|
| 10.5 | K 3.3 10% + Ag 3000 ppm | 5 | 1500 | 1:1 | Clear/ yellow |
| 10.6 | K 3.3 20% + Ag 3000 ppm | 16 | 600 | 4:1 | Clear/ colourless |

Solutions 11 to 21

Solutions 11 and 12 (Sol. 11.1 through 11.6) were prepared following the same general procedure as in Solution 10, using different metal salts and the 3.3 molar ratio potassium silicate, at varying amounts of metal and silicate.

For each formulation the appearance was noted after admixing.

Details of formulations and the results are shown in Tables 26 and 27.

TABLE 26

Mixtures of 3.3 molar ratio K silicate ("K 3.3") solutions with CuSO₄ solutions

| Sol. | Formulation | SiO₂ % | Metal ppm | Ratio silicate soln. to metal soln. | Appearance |
|---|---|---|---|---|---|
| 11.1 | K 3.3 20% + Cu 3000 ppm | 16 | 600 | 4:1 | Clear/blue |
| 11.2 | K 3.3 20% + Cu 3000 ppm | 15 | 750 | 3:1 | Clear/blue* |
| 11.3 | K 3.3 20% + Cu 3000 ppm | 13 | 1000 | 2:1 | Clear/blue* |
| 11.4 | K 3.3 20% + Cu 3000 ppm | 10 | 1500 | 1:1 | Clear/blue* |
| 11.5 | K 3.3 10% + Cu 3000 ppm | 8 | 600 | 4:1 | Clear/blue* |
| 11.6 | K 3.3 10% + Cu 1000 ppm | 5 | 500 | 1:1 | Clear/blue* |
| 11.7 | K 3.3 10% + Cu 1000 ppm | 3.3 | 667 | 1:2 | Slight haze |
| 11.8 | K 3.3 10% + Cu 1000 ppm | 2 | 800 | 1:4 | Slight haze* |

*Appearance of formulation after one week

TABLE 27

Mixtures of 3.3 molar ratio K silicate ("K 3.3") solutions with FeCl₃ solutions

| Sol. | Formulation | SiO₂ % | Metal ppm | Ratio silicate soln. to metal soln. | Appearance |
|---|---|---|---|---|---|
| 12.1 | K 3.3 10% + Fe 3000 ppm | 6.7 | 1000 | 2:1 | sludge |
| 12.2 | K 3.3 10% + Fe 1000 ppm | 5 | 500 | 1:1 | Slight haze |
| 12.3 | K 3.3 10% + Fe 1000 ppm | 3.3 | 667 | 1:2 | Slight haze |
| 12.4 | K 3.3 10% + Fe 3000 ppm | 6.7 | 1000 | 2:1 | sludge |
| 12.5 | K 3.3 10% + Fe 1000 ppm | 5 | 500 | 1:1 | Slight haze |
| 12.6 | K 3.3 10% + Fe 1000 ppm | 3.3 | 667 | 1:2 | Slight haze |

Solution 13

To 62.5 g of an aqueous solution of FeSO₄ containing 9000 ppm Fe²⁺, 46.9 g of 1M HCl (aq) and 78.1 g of de-ionized water were added, causing the pH in the solution to drop from 3.77 to 0.79.

Under vigorous stirring using a bar magnet, 2 g of the Fe²⁺ solution was added to 8 g of a solution of 3.3 SiO₂:K₂O molar ratio potassium silicate containing 10% SiO₂, to obtain Solution 21. The appearance of the formulation was observed at the end of the admixing. Details of the formulation and the results are shown in Table 25.

TABLE 28

Mixtures of 3.3 molar ratio K silicate ("K 3.3") solutions with FeSO₄ solutions

| Sol. | Formulation | SiO₂ % | Metal ppm | Ratio silicate soln. to metal soln. | Appearance |
|---|---|---|---|---|---|
| 13 | K 3.3 10% + Fe 3000 ppm | 8 | 600 | 4:1 | Clear/blue gray |

Solution 14

An aqueous solution containing 3000 ppm by weight of Ag⁺ was prepared by dissolving 0.472 g AgNO₃ in sufficient deionized water to obtain 100 g of Ag⁺ solution. Under vigorous stirring using a bar magnet, 5 g of the Ag⁺ solution was added to 5 g of a solution of 4.3 SiO₂:Na₂O molar ratio potassium silicate containing 15% SiO₂, to obtain Solution 14.1. The appearance of the formulation was observed at the end of the admixing.

Solutions 14.2 to 14.4 were prepared following the same general procedure as used to prepare Solution 14.1, but varying the concentration of either one or both of the solutions and/or the relative amounts of the solutions admixed. For each formulation the appearance was noted after admixing.

Details of the formulations and the results are shown in Table 29.

TABLE 29

Mixtures of 4.3 ratio Na silicate ("Na 4.3") solutions with AgNO₃ solutions

| Sol. | Formulation | SiO₂ % | Metal ppm | Ratio silicate soln. to metal soln. | Appearance |
|---|---|---|---|---|---|
| 14.1 | Na 4.3 15% + Ag 3000 ppm | 7.5 | 1500 | 1:1 | Slight haze |
| 14.2 | Na 4.3 10% + Ag 1000 ppm | 5 | 500 | 1:1 | Slight haze |
| 14.3 | Na 4.3 10% + Ag 1000 ppm | 8 | 200 | 4:1 | haze |
| 14.4 | Na 4.3 10% + Ag 1000 ppm | 2 | 800 | 1:4 | Clear/light yellow |

Solutions 15 and 16

Solutions 15 and 16 (Sol. 15.1 through 16.9) were prepared following the same general procedure as in Solution 14, using different metal salts and the 4.3 molar ratio sodium silicate, at varying amounts of metal and silicate. For each formulation the appearance was noted after admixing. Details of the formulations and the results are shown in Tables 30 and 31.

TABLE 30

Mixtures of 4.3 ratio Na silicate ("Na 4.3") solutions with CuSO₄ solutions

| Sol. | Formulation | SiO₂ % | Metal ppm | Ratio silicate soln. to metal soln. | Appearance |
|---|---|---|---|---|---|
| 15.1 | Na 4.3 15% + Cu 1000 ppm | 7.5 | 500 | 1:1 | Clear/blue |
| 15.2 | Na 4.3 15% + Cu 1000 ppm | 3 | 800 | 1:4 | Slight haze |
| 15.3 | Na 4.3 10% + Cu 1000 ppm | 5 | 500 | 1:1 | Slight haze |
| 15.4 | Na 4.3 10% + Cu 3000 ppm | 5 | 1500 | 1:1 | Gel/sludge |
| 15.5 | Na 4.3 10% + Cu 1000 ppm | 6.6 | 333 | 2:1 | Gel/sludge |

TABLE 31

Mixtures of 4.3 ratio Na silicate ("Na 4.3") solutions with ZnCl₂ solutions

| Sol. | Formulation | SiO₂ % | Metal ppm | Ratio silicate soln. to metal soln. | Appearance |
|---|---|---|---|---|---|
| 16.1 | Na 4.3 15% + Zn 3000 ppm | 7.5 | 1500 | 1:1 | Slight haze |
| 16.2 | Na 4.3 15% + Zn 3000 ppm | 10 | 1000 | 2:1 | Slight haze |
| 16.3 | Na 4.3 15% + Zn 3000 ppm | 3 | 2400 | 1:4 | Clear/Colourless |
| 16.4 | Na 4.3 10% + Zn 3000 ppm | 5 | 1500 | 1:1 | Clear/Colourless |
| 16.5 | Na 4.3 10% + Zn 3000 ppm | 5 | 1500 | 1:1 | Clear/Colourless |
| 16.6 | Na 4.3 10% + Zn 1000 ppm | 5 | 500 | 1:1 | Slight haze |
| 16.7 | Na 4.3 10% + Zn 1000 ppm | 5 | 500 | 1:1 | Clear/Colourless |
| 16.8 | Na 4.3 15% + Zn 1000 ppm | 7.5 | 500 | 1:1 | Clear/Colourless |
| 16.9 | Na 4.3 15% + Zn 1000 ppm | 3 | 800 | 1:4 | Clear/Colourless |

Solution 17

An aqueous solution containing 5040 ppm by weight of $Ag^+$ was prepared by dissolving 0.794 g $AgNO_3$ in sufficient deionized water to obtain 100 g of $Ag^+$ solution. Under vigorous stirring using a bar magnet, 5 g of the $Ag^+$ solution was added to 5 g of a solution of 4.3 $SiO_2:K_2O$ molar ratio potassium silicate containing 10% $SiO_2$, to obtain Solution 17.1. The appearance of the formulation was observed at the end of the admixing.

Solutions 17.2 to 17.5 were prepared following the same general procedure as used to prepare Solution 17.1, but varying the concentration of either one or both of the solutions and/or the relative amounts of the solutions admixed. For each formulation the appearance was noted after admixing. Details of the formulations and the results are shown in Table 32.

TABLE 32

Mixtures of 4.3 ratio K silicate ("K 4.3") with AgNO₃ solutions

| Sol. | Formulation | SiO₂ % | Metal ppm | Ratio silicate soln. to metal soln. | Appearance |
|---|---|---|---|---|---|
| 17.1 | K 4.3 10% + Ag 5040 ppm | 5 | 2520 | 1:1 | Clear/yellow |
| 17.2 | K 4.3 10% + Ag 3000 ppm | 3.3 | 2000 | 1:2 | Clear/yellow |
| 17.3 | K 4.3 10% + Ag 3000 ppm | 6.7 | 1000 | 2:1 | Clear/light yellow |
| 17.4 | K 4.3 15% + Ag 1000 ppm | 7.5 | 500 | 1:1 | Slight haze |
| 17.5 | K 4.3 10% + Ag 1000 ppm | 5 | 500 | 1:1 | Clear/yellow |

Solutions 18 and 19

Solutions 18 and 19 (Sol. 18.1 through 19.3) were prepared following the same general procedure as in Solution 17, using different metal salts and the 4.3 molar ratio potassium silicate, at varying amounts of metal and silicate. For each formulation the appearance was noted after admixing.

Details of the formulations and the results are shown in Tables 33 and 34.

TABLE 33

Mixtures of 4.3 ratio K silicate ("K 4.3") solutions with CuSO₄ solutions

| Sol. | Formulation | SiO₂ % | Metal ppm | Ratio silicate soln. to metal soln. | Appearance |
|---|---|---|---|---|---|
| 18.1 | K 4.3 15% + Cu 3000 ppm | 7.5 | 1500 | 1:1 | Hazy/gel |
| 18.2 | K 4.3 15% + Cu 1000 ppm | 7.5 | 500 | 1:1 | Clear/blue |
| 18.3 | K 4.3 15% + Cu 1000 ppm | 3 | 800 | 1:4 | Slight haze |

TABLE 34

Mixtures of 4.3 ratio K silicate ("K 4.3") solutions with $Zn(C_2H_3O_2)_2$ solutions

| Sol. | Formulation | SiO₂ % | Metal ppm | Ratio silicate soln. to metal soln. | Appearance |
|---|---|---|---|---|---|
| 19.1 | K 4.3 15% + Zn 3000 ppm | 7.5 | 1500 | 1:1 | Hazy/gel |
| 19.2 | K 4.3 15% + Zn 1000 ppm | 7.5 | 500 | 1:1 | Clear/colourless |
| 19.3 | K 4.3 15% + Zn 1000 ppm | 3 | 800 | 1:4 | Clear/colourless |

Solution 20

An aqueous solution containing 5040 ppm by weight of $Ag^+$ was prepared by dissolving 0.794 g $AgNO_3$ in sufficient deionized water to obtain 100 g of $Ag^+$ solution. Under vigorous stirring using a bar magnet, 5 g of the $Ag^+$ solution was added to 5 g of a solution of 4.3 $SiO_2:Li_2O$ molar ratio lithium silicate containing 15% $SiO_2$, to obtain Solution 20.1. The appearance of the formulation was observed at the end of the admixing.

Solutions 20.2 to 20.6 were prepared following the same general procedure as used to prepare Solution 20.1, but varying the concentration of either one or both of the solutions and/or the relative amounts of the solutions admixed. For each formulation the appearance was noted after admixing. Details of the formulations and the results are shown in Table 35.

TABLE 35

Mixtures of 4.3 ratio Li silicate solutions with AgNO₃ solutions

| Sol. | Formulation | SiO₂ % | Metal ppm | Ratio silicate soln. to metal soln. | Appearance |
|---|---|---|---|---|---|
| 20.1 | Li 4.3 15% + Ag 5040 ppm | 7.5 | 2520 | 1:1 | Haze/dark |
| 20.2 | Li 4.3 15% + Ag 3000 ppm | 7.5 | 1500 | 1:1 | Haze/dark |
| 20.3 | Li 4.3 15% + Ag 1000 ppm | 7.5 | 500 | 1:1 | Haze/precipitate |
| 20.4 | Li 4.3 10% + Ag 1000 ppm | 5 | 500 | 1:1 | Haze/precipitate |
| 20.5 | Li 4.3 10% + Ag 1000 ppm | 6.7 | 333 | 2:1 | Haze/precipitate |
| 20.6 | Li 4.3 10% + Ag 1000 ppm | 3.3 | 666 | 1:2 | Clear/yellow |

Solutions 21 and 22

Solutions 21 and 22 (Sol. 21.1 through 22.3) were prepared following the same general procedure as in Solution 20, using different metal salts and the 4.3 molar ratio lithium silicate, at varying amounts of metal and silicate. For each formulation the appearance was noted after admixing. Details of the formulations and the results are shown in Tables 36 and 37.

TABLE 36

Mixtures of 4.3 ratio Li silicate solutions with CuSO₄ solutions

| Sol. | Formulation | SiO₂ % | Metal ppm | Ratio silicate soln. to metal soln. | Appearance |
|---|---|---|---|---|---|
| 21.1 | Li 4.3 15% + Cu 3000 ppm | 7.5 | 1500 | 1:1 | Haze, blue. Almost clear the day after |
| 21.2 | Li 4.3 15% + Cu 1000 ppm | 7.5 | 500 | 1:1 | Clear, blue |
| 21.3 | Li 4.3 15% + Cu 1000 ppm | 3 | 800 | 1:4 | Clear, blue |

TABLE 37

Mixtures of 4.3 ratio Li silicate solutions with Zn(C₂H₃O₂)₂ solutions

| Sol. | Formulation | SiO₂ % | Metal ppm | Ratio silicate soln. to metal soln. | Appearance |
|---|---|---|---|---|---|
| 22.1 | Li 4.3 15% + Zn 3000 ppm | 7.5 | 1500 | 1:1 | Haze, gel |
| 22.2 | Li 4.3 15% + Zn 1000 ppm | 7.5 | 500 | 1:1 | Clear, colorless |
| 22.3 | Li 4.3 15% + Zn 1000 ppm | 3 | 800 | 1:4 | Clear, colorless |

Solution 23

An aqueous solution containing 5040 ppm by weight of Ag⁺ was prepared by dissolving 0.794 g AgNO₃ in sufficient deionized water to obtain 100 g of Ag⁺ solution. Under vigorous stirring using a bar magnet, 5 g of the Ag⁺ solution was added to 5 g of a solution of 2.5 SiO₂:Na₂O molar ratio sodium silicate containing 10% SiO₂, to obtain Solution 23.1. The appearance of the formulation was observed at the end of the admixing.

Solutions 23.2 to 23.5 were prepared following the same general procedure as used to prepare Solution 23.1, but varying the concentration of either one or both of the solutions and/or the relative amounts of the solutions admixed. For each formulation the appearance was noted after admixing. Details of the formulations and the results are shown in Table 39.

TABLE 39

Mixtures of 2.5 ratio Na silicate ("Na 2.5") solutions with AgNO₃ solutions

| Sol. | Formulation | SiO₂ % | Metal ppm | Ratio silicate soln. to metal soln. | Appearance |
|---|---|---|---|---|---|
| 23.1 | Na 2.5 10% + Ag 5040 ppm | 5 | 2520 | 1:1 | Sediment/yellow |
| 23.2 | Na 2.5 10% + Ag 3000 ppm | 5 | 1500 | 1:1 | Sediment/yellow |
| 23.3 | Na 2.5 10% + Ag 1000 ppm | 6.7 | 333 | 2:1 | Precipitation/light yellow |
| 23.4 | Na 2.5 10% + Ag 1000 ppm | 3.3 | 667 | 1:2 | Precipitation/light brown |
| 23.5 | Na 2.5 10% + Ag 1000 ppm | 8 | 200 | 4:1 | Clear/colourless |

Solutions 24 and 25

Solutions 24 and 25 (Sol. 24.1 through 25.4) were prepared following the same general procedure as in Solution 23, using different metal salts and the 2.5 molar ratio sodium silicate, at varying amounts of metal and silicate. For each formulation the appearance was noted after admixing. Details of the formulations and the results are shown in Tables 40 and 41.

TABLE 40

Mixtures of 2.5 ratio Na silicate ("Na 2.5") solutions with CuSO₄ solutions

| Sol. | Formulation | SiO₂ % | Metal ppm | Ratio silicate soln. to metal soln. | Appearance |
|---|---|---|---|---|---|
| 24.1 | Na 2.5 10% + Cu 3000 ppm | 5 | 1500 | 1:1 | Clear/blue |

TABLE 41

Mixtures 2.5 ratio Na silicate ("Na 2.5") solutions with Zn(C₂H₃O₂)₂ solutions

| Sol. | Formulation | SiO₂ % | Metal ppm | Ratio silicate soln. to metal soln. | Appearance |
|---|---|---|---|---|---|
| 25.1 | Na 2.5 10% + Zn 3000 ppm | 5 | 1500 | 1:1 | Slight haze |
| 25.2 | Na 2.5 10% + Zn 1000 ppm | 5 | 500 | 1:1 | Clear/colourless |
| 25.3 | Na 2.5 5% + Zn 500 ppm | 2.5 | 250 | 1:1 | Clear/colourless |
| 25.4 | Na 2.5 10% + Zn 3000 ppm | 5 | 1500 | 1:1 | Slight haze |

Solution 26

An aqueous solution containing 1000 ppm by weight of Ag⁺ was prepared by dissolving 0.157 g AgNO₃ in sufficient deionized water to obtain 100 g of solution. Separately, 10 g of a solution of 3.3 SiO₂:Li₂O molar ratio lithium silicate containing 10% SiO₂ were mixed with 10 g of a solution of 3.3 SiO₂:K₂O molar ratio potassium silicate containing 10%

$SiO_2$. To 5 g of the obtained mixed alkali silicate solution, 5 g of the silver containing solution were added, dropwise and under stirring, to obtain Solution 26.1. After completion of the addition, the appearance of the formulation was noted.

Solutions 26.2 and 26.3 were prepared following the same general procedure as used to prepare Solution 26.1, but varying the alkali silicate solutions used. For each formulation, the appearance was noted after admixing. Details of the formulations and the results are shown in Table 38.

TABLE 42

Mixtures of blends of alkali silicate solutions with $AgNO_3$ solutions

| Sol. | Formulation | $SiO_2$ % | Metal ppm | Ratio silicate soln. to metal soln. | Appearance |
| --- | --- | --- | --- | --- | --- |
| 26.1 | K 3.3 + Li 3.3 + Ag 1000 ppm | 5 | 500 | 1:1 | Clear/light yellow |
| 26.2 | Na 3.3 + Li 3.3 + Ag 1000 ppm | 5 | 500 | 1:1 | Clear/light yellow, slight haze |
| 26.3 | Na 2.5 + Li 3.3 + Ag 1000 ppm | 5 | 500 | 1:1 | Clear/light yellow, slight haze |

Solutions 27 and 28

Solutions 27 and 28 (Sol. 27.1 through 28.3) were prepared following the same general procedure as used in Solution 26, but using other metal salts. For each formulation, the appearance was noted after admixing. Details of the formulations and the results are shown in Tables 43 and 44.

TABLE 43

Mixtures of blends of alkali silicate solutions with $CuSO_4$ solutions

| Sol. | Formulation | $SiO_2$ % | Metal ppm | Ratio silicate soln. to metal soln. | Appearance |
| --- | --- | --- | --- | --- | --- |
| 27.1 | K 3.3 + Li 3.3 + Cu 1000 ppm | 5 | 500 | 1:1 | Clear/blue |
| 27.2 | Na 3.3 + Li 3.3 + Cu 1000 ppm | 5 | 500 | 1:1 | Clear/blue |
| 27.3 | Na 2.5 + Li 3.3 + Cu 1000 ppm | 5 | 500 | 1:1 | Clear/blue |

TABLE 44

Mixtures of blends of alkali silicate solutions with $Zn(C_2H_3O_2)_2$ solutions

| Sol. | Formulation | $SiO_2$ % | Metal ppm | Ratio silicate soln. to metal soln. | Appearance |
| --- | --- | --- | --- | --- | --- |
| 28.1 | K 3.3 + Li 3.3 + Zn 1000 ppm | 5 | 500 | 1:1 | Clear, some preciptiation |
| 28.2 | Na 3.3 + Li 3.3 + Zn 1000 ppm | 5 | 500 | 1:1 | Clear/colourless |
| 28.3 | Na 2.5 + Li 3.3 + Zn 1000 ppm | 5 | 500 | 1:1 | Clear/colourless |

Solution 29

Solutions 1.5 and 3.2 were repeated, but to the solutions were also added a small amount of a non-ionic surfactant, viz. Empilan® PF 7179 at an amount of 0.2% by weight of the final solution, to give the solutions of Solutions 29.1 and 29.2, respectively. The mixtures were observed directly after admixing. Details of the formulations and the results are shown in Table 45.

TABLE 45

Mixtures containing 0.2% of the non-ionic surfactant Empilan ® PF 7169

| Sol. | Formulation | $SiO_2$ % | Metal ppm | Ratio silicate soln. to metal soln. | Appearance |
| --- | --- | --- | --- | --- | --- |
| 29.1 | Li 3.3 10% + Cu 3000 ppm | 8 | 600 | 4:1 | Clear, blue |
| 29.2 | Li 3.3 10% + Zn 3000 ppm | 5 | 1500 | 1:1 | Clear, colourless |

The metal containing silicate solution as provided herein is remarkably stable, and preferably is free from any complexing agent for the ions of metal or contains complexing agent(s) for the ions of metal in a total molar ratio of complexing agent(s) to such ions of lower than 1:100.

The colloidal dispersions provided herein have been tested in different settings for use in methods to reduce odors, as described herein below.

Example 1

A house in Svedala, Sweden, had a bad smell detected. The smell came from a cat litter box that used to be placed in the upstairs bathroom, and the smell did not go away even after careful cleaning. After spraying, in the bathroom, a colloidal dispersion of 5 nm particles, containing 300 ppm $Cu^{2+}$ and 5% $SiO_2$, the smell disappeared immediately and permanently.

Example 2

Nordsjällands elementary school is located in Kokkedal on Zealand, Denmark, and has around 1500 students. The school building was built in 1988 and had had a problem with bad smell in the students' restrooms for a long time. The restrooms are about 25 $m^2$ with tiled floors and walls.

Toilets with a strong smell or urine were cleaned and thereafter the entire restrooms were treated with a colloidal dispersion of 5 nm particles, containing 300 ppm $Cu^{2+}$ and 5% $SiO_2$, which was applied with a fogger. The smell disappeared immediately after the treatment and the restroom has been odor free for two months since the treatment. Both students and school personnel have noticed a great improvement of the air quality in the restrooms.

Example 3

Norsk Protein AS is the leading facility in Norway for treatment of animal waste originating from life stock and the meat industry. The modern facility employs reactors and evaporators to recover valuable protein powder and industrial fat. Although the process is contained within closed reactors, tanks and pipes, and while effluent gases and liquids are adequately treated, odor is apparent at various parts of the production facility.

A colloidal dispersion of 5 nm particles, containing 300 ppm $Cu^{2+}$ and 5% $SiO_2$, was sprayed into the air in a locker room in the factory and at a process water pump station at the facility. The smell disappeared immediately.

Example 4

Tests of the odor reducing activity of a colloidal dispersion of 5 nm particles, containing 300 ppm $Cu^{2+}$ and 5% $SiO_2$, were performed using two different synthetic odorous compounds, viz. diacetyl and guaiacol. Diacetyl (IUPAC name: butanedione or butane-2,3-dione), CAS No: 431-03-8, is a vicinal diketone of the formula $(CH_3CO)_2$. Diacetyl is formed during fermentation and occurs naturally in butter, cream, beer, wine (Chardonnay) and whiskey. Guaiacol, of formula $C_6H_4(OH)(OCH_3)$ (IUPAC name: 2-methoxyphenol), CAS No: 90-05-1, is a naturally occurring organic compound found in smoke from wood, imparting the smokey flavor to whiskey and roasted coffee.

Circular patches of 4.5 cm in diameter were cut from a multi-layer polyester nonwoven fabric weighing about 250 grams per square meter. Using the equation for the area of a circle, i.e. $A=\pi r^2$, the surface area of each patch was calculated to approximately $1.6 \times 10^{-3}$ $m^2$, which gave a weight of about 0.4 g for each patch. To each patch, 3 g of the liquid colloidal dispersion were applied, viz. the dispersion was applied at a surface concentration of about 1.9 $kg/m^2$. The patches were allowed to dry over night. After drying, each patch weighed about 1.75 g.

The thus treated patches were tested by placing each patch in a beaker containing 3 ml of diacetyl and guaiacol. The patches were not allowed to come into direct contact with the liquid, and the beaker was covered with a polyethylene membrane. As a reference, non-treated patches of same surface area were placed in beakers containing 3 ml of diacetyl and guaiacol. The concentration of the odorous compounds in the gas phase within the beaker was determined for each type of patch (test patch and reference patch). In the presence of colloidal dispersion of the invention, the concentration of diacetyl in the gas phase had been reduced by 49%, compared to the concentration in the presence of the non-treated patch, whereas the concentration of guaiacol had been reduced by 41% as measured by gas chromatography (GC).

Example 5

The test of Example 4 was repeated, using diacetyl, guaiacol, 3-methylbutanal (3-MB, CAS No. 590-86-3) and dimethyl trisulfide (DMTS, CAS No. 3658-80-8) as test compounds, and using:

(a) an aqueous colloidal dispersion of 5 nm particles, containing 300 ppm $Cu^{2+}$, and 5% $SiO_2$, (b) an aqueous colloidal dispersion of 5 nm particles, containing 300 ppm $Zn^{2+}$, and 5% $SiO_2$, or (c) an aqueous colloidal dispersion of 5 nm particles, containing 300 ppm $Fe^{2+}$, and 5% $SiO_2$.

The results showed that (a), (b) and (c) were all effective against diacetyl and 3-methylbutanal. Formulation (a) was the most effective against diacetyl, guaiacol and dimethyl trisulfide, with a reduction of the gas phase concentration of about 50%, about 40%, and about 5% respectively, while formulation (b) was the most effective against 3-methylbutanal, with a 40% reduction of the gas phase concentration, while formula (a) provided a reduction of about 20%. The formulation (c) provided a reduction of about 25% of the diacetyl concentration, and about 30% of the 3-methylbutanal concentration.

Example 6

Denim test samples were used. The samples were treated with an aqueous colloidal dispersion of 5 nm particles, containing 300 ppm $Cu^{2+}$, and 5% $SiO_2$ in a set-up described in FIG. 1. The samples were then divided into 2 groups: one group of test samples were used without any further treatment (Denim/Non-Wash). The other group of denim samples was submitted to 20 wash cycles (Denim/Wash-20). The deodorization properties of the formulation were then tested according to the ISO 17299 standard using a detector tube method and a gas chromatography (GC) method. For the detector tube method, a sample size of 100 $cm^2$ of the fabric was used, and for the GC method, a sample size of 50 $cm^2$ was used. In each case, the remaining gas concentration was measured after 2 h of contact with the formulation. The test was performed using ammonia, hydrogen sulfide and isovaleric acid as odorants, at an initial concentration of 100 ppm, 4 ppm, and about 38 ppm, respectively, and test results were expressed as reduction (%) of odorant concentration in the gas phase. The results show the efficacy of the formulations even after 20 wash cycles, cf. Table 46.

TABLE 46

| Odorant | Denim/Non-Wash | Denim/Wash-20 |
| --- | --- | --- |
| Ammonia | 98 | 73 |
| Hydrogen sulfide | 68 | 58 |
| Isovaleric acid | ≥99 | ≥99 |

Example 7

Textile cloths were drenched with butyric acid and ammoniac and allowed to dry. An aqueous silicate solution according to the invention, containing 600 ppm Cu, was sprayed onto some of the cloths either 3 times or 10 times. A test panel was able to easily distinguish between cloths that had received treatment and cloths that had received no treatment, the odor from the cloths treated by the silicate solution of the invention was substantially reduced.

The invention claimed is:

1. A method for reducing odor, comprising
providing a stable colloidal dispersion of particles of silica having a particle size of from 3 nm to 100 nm, said particles having ions of one or more metals selected from copper, silver, zinc and iron adsorbed at the particle surface, wherein said metal ions are present at a total concentration of from 0.05 mM to 50 mM, and bringing at least one of said particles into contact with an odorous compound.

2. The method according to claim 1, wherein the odorous compound is present in a gaseous phase.

3. The method according to claim 2, wherein the at least one particle is brought into contact with the odorous compound by spraying the dispersion into the gaseous phase.

4. The method according to claim 2, wherein the at least one particle is brought into contact with the odorous compound by applying the dispersion to a solid surface and allowing the solid surface to come into contact with the gaseous phase.

5. The method according to claim 1, wherein the odorous compound is present in a liquid phase.

6. The method according to claim 1, wherein said ions are present at the surface in an amount of 0.0005-5 ions per $nm^2$ of silica particle surface.

7. The method according to claim 6, wherein said ions are present at the surface in an amount of 0.01-0.5 ions per $nm^2$ of silica particle surface.

8. The method according to claim 1, wherein the surface of the particles of silica contains aluminosilicate sites.

9. The method according to claim 1, wherein said ions are present at a total concentration of from 1 ppm to 3000 ppm by weight of the dispersion.

10. The method according to claim 1, wherein the dispersion has a pH of from 8 to 11.

11. The method according to claim 1, wherein said particles of silica are present at a concentration of from 0.001% by weight to 25% by weight of the dispersion.

12. The method according to claim 1, wherein the one or more metals are selected from iron, copper and zinc.

* * * * *